US007901683B2

(12) United States Patent
Griswold-Prenner et al.

(10) Patent No.: US 7,901,683 B2
(45) Date of Patent: *Mar. 8, 2011

(54) METHODS OF INHIBITING AMYLOID TOXICITY

(75) Inventors: Irene Griswold-Prenner, San Francisco, CA (US); Sarah Wright, San Francisco, CA (US); Theodore Yednock, Forest Knolls, CA (US); Russell Rydel, Belmont, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/336,340

(22) Filed: Dec. 16, 2008

(65) Prior Publication Data
US 2009/0220505 A1 Sep. 3, 2009

Related U.S. Application Data

(62) Division of application No. 10/190,548, filed on Jul. 9, 2002, now Pat. No. 7,517,525.

(60) Provisional application No. 60/341,772, filed on Dec. 17, 2001, provisional application No. 60/304,315, filed on Jul. 9, 2001.

(51) Int. Cl.
A61K 39/395 (2006.01)
(52) U.S. Cl. ............. 424/142.1; 424/133.1; 424/141.1; 424/152.1
(58) Field of Classification Search .............. None
See application file for complete search history.

(56) References Cited

U.S. PATENT DOCUMENTS

| | | | |
|---|---|---|---|
| 5,612,486 A | 3/1997 | McConlogue et al. |
| 5,753,230 A | 5/1998 | Brooks et al. |
| 5,849,865 A | 12/1998 | Cheng et al. |
| 5,985,278 A | 11/1999 | Mitjans et al. |
| 6,469,024 B2 | 10/2002 | Li et al. |
| 6,743,427 B1 | 6/2004 | Schenk |
| 7,517,525 B2 | 4/2009 | Prenner et al. |
| 2002/0160954 A1 | 10/2002 | Hageman et al. |
| 2003/0040044 A1 | 2/2003 | Heavner et al. |
| 2003/0202977 A1 | 10/2003 | Amin et al. |
| 2004/0259152 A1 | 12/2004 | Murray et al. |
| 2008/0193444 A1 | 8/2008 | Wright et al. |

FOREIGN PATENT DOCUMENTS

| | | |
|---|---|---|
| EP | 0 719 859 A1 | 7/1996 |
| WO | WO 98/15179 A1 | 4/1998 |
| WO | WO 99/27944 A1 | 6/1999 |
| WO | WO 99/37683 A1 | 7/1999 |
| WO | WO 00/44404 A2 | 8/2000 |
| WO | WO 00/66730 A2 | 11/2000 |
| WO | WO 03/006893 A2 | 1/2003 |
| WO | WO 2008/116100 A1 | 8/2008 |

OTHER PUBLICATIONS

U.S. Appl. No. 11/723,745, filed Mar. 21, 2007.
U.S. Appl. No. 60/341,772, filed Dec. 17, 2001.
U.S. Appl. No. 60/304,315, filed Jul. 9, 2001.
Adams, "Collagen Gene Expression," Am. J. Respir. Cell. Molec. Biol., 1:161-168 (1989).
Alberts et al., *Molecular Biology of the Cell*, 3rd Edition, pp. 129-130 (1994).
Akiyama et al, Immunohistochemical localization of vitronectin, its receptor and beta-3 integrin in Alzheimer brain tissue, *J. Neuroimmunol.*, 32(1):19-28 (1991).
ATTC Accession HB-8448, L230 Monoclonal antibody (accessed 2006).
Bamberger et al., A cell surface receptor complex for fibrillar beta-amyloid mediates microglial activation, *J. Neurosci.*, 23:(7):2665-2674 (2003).
Bard, F. et al., *Nature Medicine*, 6(8):916-919(2000).
Basler et al., "Scrapie and Cellular PrP Isoforms Are Encoded by the Same Chromosomal Gene," *Cell*, 46:417-428 (1986).
Batt et al., "Disubstituted Indazoles as Potent Antagonists ofIntegrin alphaVbeta3," *Journal of Medicinal Chemistry*, 43:41-58 (2000).
BOLTONet al., "Identification of a Protein That Purifies with the Scrapie Prion", *Science*, 218:1309-1311(1982).
Borchelt et al., "Accelerated Amyloid Deposition in the Brains of Transgenic Mice Coexpressing Mutant Presenilin 1 and Amyloid Precursor Proteins," *Neuron*, 19:939-945 (1997).
Bronfman et al., "Laminin Blocks the Assembly of Wild-Type AP and the Dutch Variant Peptide into Alzheimer's Fibrils," *Amyloid: Int. J. Exp. Clin. Invest.* 5, 5:16-23 (1998).
Chartier-Harlin et al., "Early-Onset Alzheimer's Disease Caused by Mutations at Codon 717 of the β-Amyloid Precursor Protein Gene," *Nature*, 353:844-846 (1991).
Castillo et al., "Laminin Inhibition of β-Amyloid Protein (AP) Fibrillogenesis and Identification of An AP Binding Site Localized to the Globular Domain Repeats on the Laminin A Chain," *J. Neurosci. Res.*, 62:451-462 (2000).
Chemicon Antibody Information Sheet, Mouse Anti-Human Integrin αV Monoclonal Antibody, dated Aug. 1998.
Cheresh et al, "Human Endothelial Cells Synthesize and Express an Arg-Gly-Asp-directed Adhesion Receptor Involved in Attachment of Fibrinogen and Von Willebran Factor,," *PNAS*, 84:6471-6475 (1987).
Chesebro et al., "Identification of Scrapie Prion Protein-Specific mRNA in Scrapie-Infected and Uninfected Brain," *Nature*, 315:331-333 (1985).
Choh, "β-Endorphin Omission Analogs: Dissociation of Immunoreactivity From Other Biological Activates," *PNAS*, 77(6):3211-3214 (1990).
Chung et al., "Parkin Ubiquitinates the a-Synuclein-Interacting Protein, Synphilin-1: Implications for Lewy-Body Formation in Parkinson Disease," *Nature Medicine*, 7:1144 1150 (2001).
Cooper et al., "Amylin Found in Amyloid Deposits in Human Type 2 Diabetes Mellitus May be a Hormone that Regulates Glycogen Metabolism in Skeletal Muscle." *Proc. Natl. Acad. Sci. USA*, 85:7763-7766 (1988).

(Continued)

*Primary Examiner* — Daniel E. Kolker
(74) *Attorney, Agent, or Firm* — Alston & Bird LLP

(57) ABSTRACT

The present invention features methods and compositions for inhibiting amyloidogenic protein toxicity, inhibiting formation of an amyloidogenic protein deposit and/or treating amyloidogenic diseases by administering a pharmaceutically effective amount of one or more agents that bind an integrin or an integrin subunit.

21 Claims, 17 Drawing Sheets

OTHER PUBLICATIONS

Coulson et al., Down-regulation of the amyloid protein precursor of Alzheimer's disease by antisense oligonucleotides reduces neuronal adhesion to specific substrata, Brain Res., 770(1-2):72-80 (1997).

Eikelenboom et al., Cellular and substrate adhesion molecules (integrins) and their ligands in cerebral amyloid plaques in Alzheimer's disease, Virchows Arch., 424(4): 421-427 (1994).

El Khoury et a/., "Scavenger Receptor-Mediated Adhesion of Microglia to p-Amyloid Fibrils," Nature, 382:716-719 (1996).

Friedlander et al., "Migration of Brain Tumor Cells on Extracellular Matrix Proteins in Vitro Correlates with Tumor Type and Grade and Involves $\alpha_v$ and $\beta_1$ Integrins[1]," Cancer Research, 56:1939-1947 (1996).

Ghiso et al., "A 109-Amino-Acid C-Terminal Fragment of Alzheimer's-Disease Amyloid Precursor Protein Contains a Sequence, -RHDS-, that Promotes Cell Adhesion," Biochem. J., 288:1053-1059 (1992).

Giese et al., "Prion-Induced Neuronal Damage—The Mechanisms of Neuronal Destruction in the Subacute Spongiform Encephalopathies in the Mechanisms of Neuronal Damage in Virus Infections of the Nervous System (Gosztony, 6.ed.)," Springer-Verlag, pp. 204-27 (2001).

Goate et al., "Segregation of a Missense Mutation in the Amyloid Precursor Protein Gene with Familial Alzheimer's Disease," Nature, 349:704-706 (1991).

Hardy, "Amyloid, the Presenilins and Alzheimer's Disease," Trends Neurosci., 20:154-159 (1997).

Harlow et al., Antibodies: A laboratory Manual, 7-10 (1988).

Henthorn et al., "Active Transport of Fentanyl by the Blood-Brain Barrier[1]," Journal of Pharmacology and Experimental Therapeutics, 289:1084-1089 (1999).

Hsiao et a/., "Correlative Memory Deficits, AfJ Elevation, and Amyloid Plaques in Transgenic Mice", Science, 274:99-102 (1996).

Hund et a/., "Transthyretin-Associated Neuropathic Amyloidosis," Neurology, 56:431-435 (2001).

Hynes, "Integrins: Versatility, Modulation, and Signaling in Cell Adhesion," Cell, 69: 11-25 (1992).

Johnson et al., "Islet Amyloid Polypeptide: Mechanisms of Amyloidogenesis in the Pancreatic Islets and Potential Roles in Diabetes Mellitus", Laboratory Investigation, 66:522-535 (1992).

Kahn et a/., "Islet Amyloid: A Long-Recognized but Underappreciated Pathological Feature of Type 2 Diabetes," Diabetes, 48:241-253 (1999).

Kang et a/., "The Precursor of Alzheimer's Disease Amyloid A4 Protein Resembles a Cell-Surface Receptor," Nature, 325:733-736 (1987).

Kawahara, E. et al., American Journal of Pathology, 134(6):1305-1314 (1989).

Kellings et al., "Further Analysis of Nucleic Acids in Purified Scrapie Prion Preparations by Improved Return Refocusing Gel Electrophoresis," Journal of General Virology, 73:1025-1029 (1992).

Kitaguchi et al., "Novel Precursor of Alzheimer's Disease Amyloid Protein Shows Protease Inhibitory Activity," Nature, 331:530-532 (1988).

Kuby et al., Immunology, $3^{rd}$ Edition: p. 123 (1997).

Leighton et al., "Pancreatic Amylin and Calcitonin Gene-Related Peptide Cause Resistance to Insulin in Skeletal Muscle In Vitro," Nature, 335:632-635 (1988).

Matsubara et al., Association between diabetic retinopathy and genetic variations in $\alpha 1\beta 2$ integrin, a platelet receptor for collagen, Blood, 95(5):1560-1564 (2000).

Matter et al., "The a5p1 Integrin Mediates Elimination of Amyloid-P Peptide and Protects Against Apoptosis," The Journal of Cell Biology, 141:1019-1030 (1998).

McGeer et al., "Innate Inflammatory Reaction of the Brain in Alzheimer Disease," MJM, 3:134-141 (1997).

Monning et al., "Extracellular matrix influences the biogenesis of amyloid precursor protein in microglial cells," J. Bioi Chem., 270(13):7104-7110 (1995).

Mullan et al., "A Pathogenic Mutation for Probable Alzheimer's Disease in the APP Gene at the NTerminus of β-Amyloid," Nature Genetics, 1:345-347 (1992).

Murrell et al., "A Mutation in the Amyloid Precursor Protein Associated with Hereditary Alzheimer's Disease," Science, 254:97-99 (1991).

Murtomaki et al., "Laminin and Its Neurite Outgrowth-Promoting Domain in the Brain in Alzheimer's Disease and Down's Syndrome Patients," J. Neurosci. Res., 32:261-273 (1992).

Oesch et al., "A Cellular Gene Encodes Scrapie PrP 27-30 Protein," Cell, 40:735-746 (1985).

Osborn, "Leukocyte Adhesion to Endothelium in Inflammation," Cell, 62:3-6 (1990).

Pan et al., "Conversion of α-Helices into p-Sheets Features in the Formation of the Scrapie Prion Proteins," Proc. Natl. Acad. Sci. USA, 90:10962-10966 (1993).

Paresce et al., "Microglial Cells Internalize Aggregates of the Alzheimer's Disease Amyloid β-Protein Via a Scavenger Receptor," Neuron, 17:553-565 (1996).

PCT International Search Report mailed Aug. 11, 2008 for application PCT/US08/57713.

PCT International Search Report May 27, 2003 for application PCT/US03/19803.

PCT International Preliminary Report on Patentability of Sep. 22, 2009 for application PCT/US08/57713.

PCT Written Opinion mailed Aug. 11, 2008 for application PCT/US08/57713.

Ponte et al., "A New A4 Amyloid mRNA Contains a Domain Homologous to Serine Proteinase Inhibitors," Nature, 331:525-527 (1988).

Prusiner, "Novel Proteinaceous Infectious Particles Cause Scrapie," Science, 216:136-144 (1982).

Prusiner et al., "Purification and Structural Studies of a Major Scrapie Prion Protein," Cell, 38:127-134 (1984).

Prusiner, "Genetic and Infectious Prion Diseases," Arch. Neural., 50:1129-1153 (1993).

Prusiner, "Prions," Proc. Natl. Acad. Sci. USA, 95:13363-13383 (1998).

Riesner et al., "Prions and Nucleic Acids: Search for <<Residual>> Nucleic Acids and Screening for Mutations in the PrP-Gene," Dev. Biol. Stand., 80:173-181 (1993).

Sabo et al., Neuroscience Letters, 18(4):25-28 (1995).

Skolnick et al., "From Genes to Protein Structure and Function: Novel Applications of Computational Approaches in the Genomic Era," Trends in Biotech, 18(1):34-39 (2000).

Springer, "Adhesion Receptors of the Immune System," Nature, 346:425-434 (1990).

Sthal et al., "Structural Studies of the Scrapie Prion Protein Using Mass Spectrometry and Amino Acid Sequencing," Biochemistry, 32:1991-2002 (1993).

Sturchler-Pierrat et al., "Two Amyloid Precursor Protein Transgenic Mouse Models with Alzheimer Disease-Like Pathology," Proc. Natl. Acad. Sci. USA, 94:13287-13292 (1997).

Tsai et al., "Platelet collagen receptor a1β2 integrin and glycoprotein lila PI(A1/A2) polymorphisms are not associated with nephropathy in type 2 diabetes," Am. J. Kidney Dis., 38(6):1185-1190 (2001).

Velez-Pardo et al., "Familial Alzheimer's Disease: Oxidative Stress, β-Amyloid, Presenilins, and Cell Death," Gen. Pharmac., 31:675-681 (1998).

Wang et al., "β-Amyloid$_{1-42}$ Binds to α7 Nicotinic Acetylcholine Receptor with High Affinity," The Journal of Biological Chemistry, 275:5626-5632 (2000).

Wang et al., "Amyloid Peptide Aβ$_{1-42}$ Binds Selectively and with Picomolar Affinity to α7 Nicotinic Acetylcholine Receptors," J. Neurochem., 75:1155-1161 (2000).

Wright et al., "alpha2betal and alphaVbetal integrin signaling pathways mediate amyloid-1-19 and 25-62 beta-induced neurotoxicity," Neurobiology of Aging, 28: 226-237 (2006).

Yaar et al., "Binding of β-Amyloid to the p75 Neurotrophin Receptor Induces Apoptosis," The Journal of Clinical Investigation, 100:2333-2340 (1997).

Yan et al., "RAGE and Amyloid-β Peptide Neurotoxicity in Alzheimer's Disease," Nature, 382:685-691 (1996).

Yan et al., "An Intracellular Protein that Binds Amyloid-β Peptide and Mediates Neurotoxicity in Alzheimer's Disease," Nature, 389:689-695 (1997).

Yamazaki et al, "Cell Surface Amyloid β-Protein Precursor Colocalizes with β1 Intergrins at Substrate Contact Sites in Neural Cells," *J. of Neuroscience*, 17(3):1004-1010 (1997).

Zlokovic et al., "Cerebrovascular Permeability to Peptides: Manipulations of Transport Systems at the Blood-Brain Barrier," *Pharmaceutical Research*, 12:1395-1406 (1995).

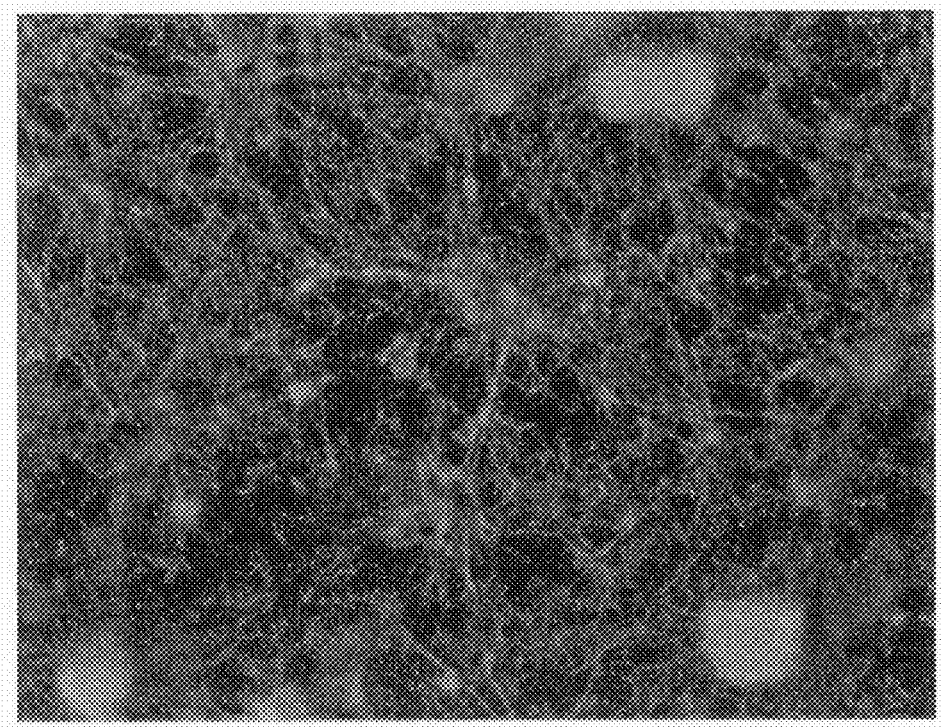
FIG. 1
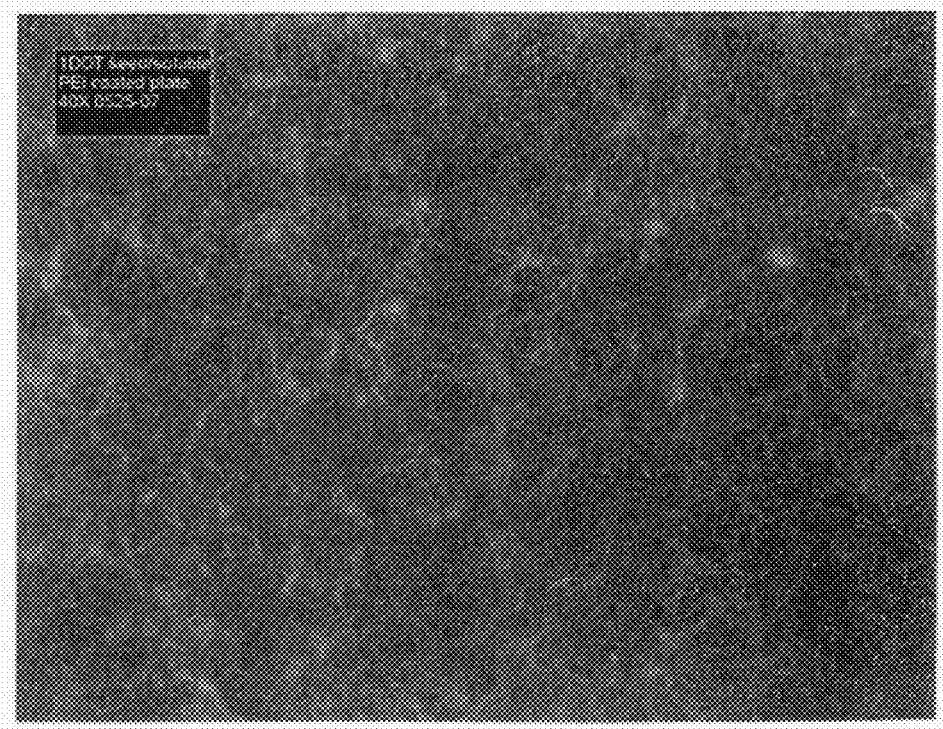

←β1

β1 Integrin Ip

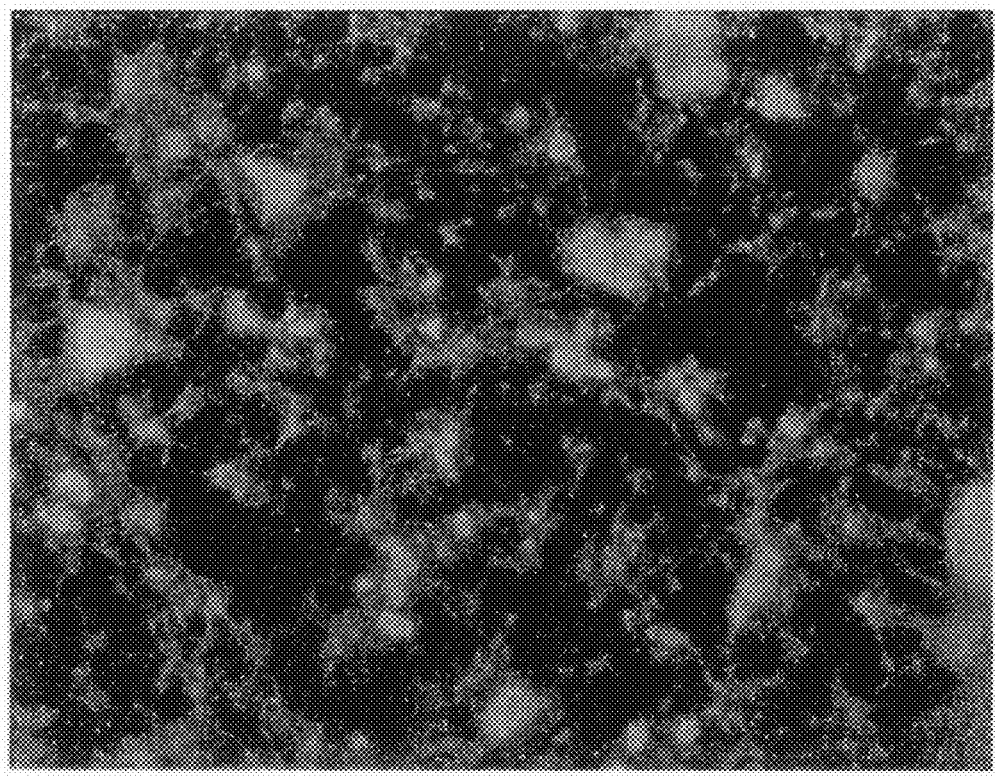
FIG. 2B
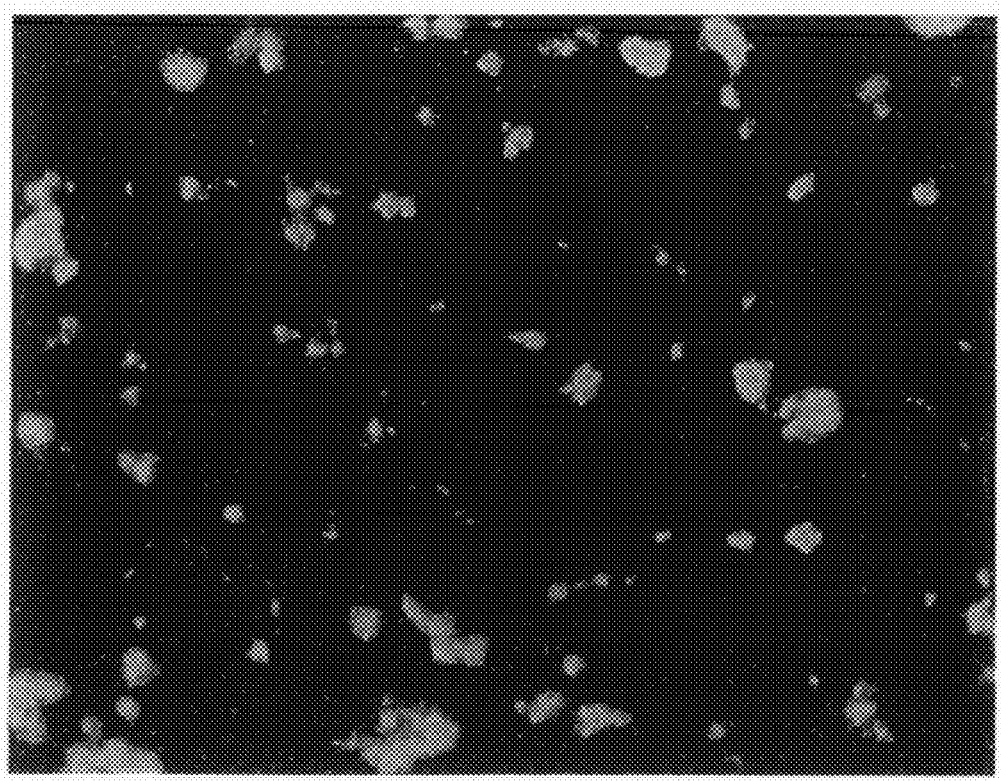

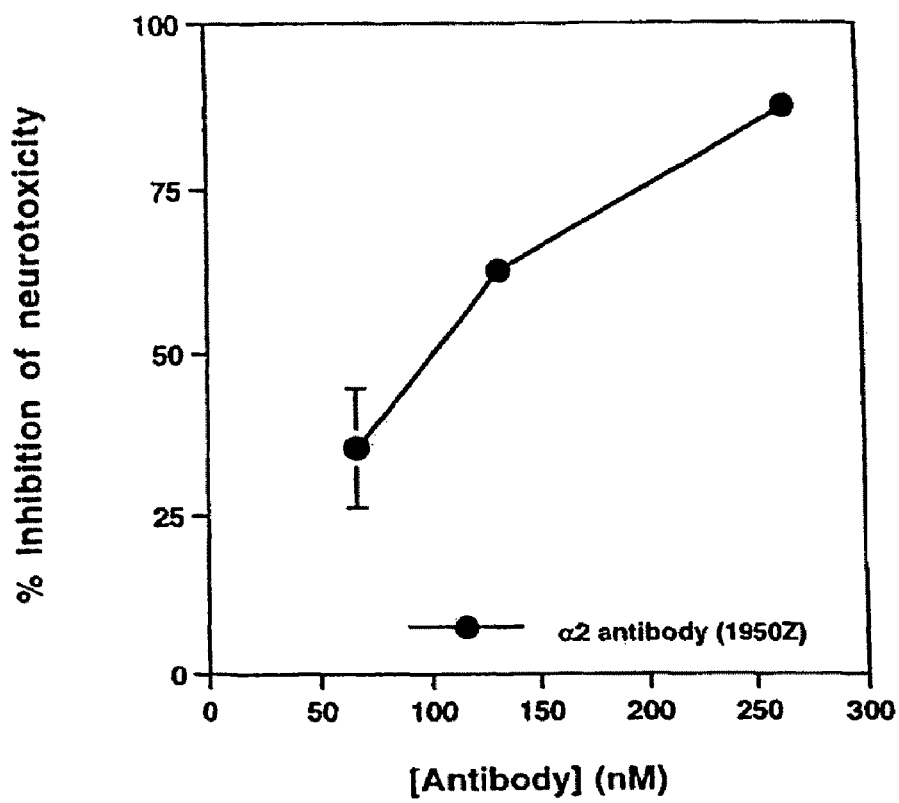
FIG. 3C
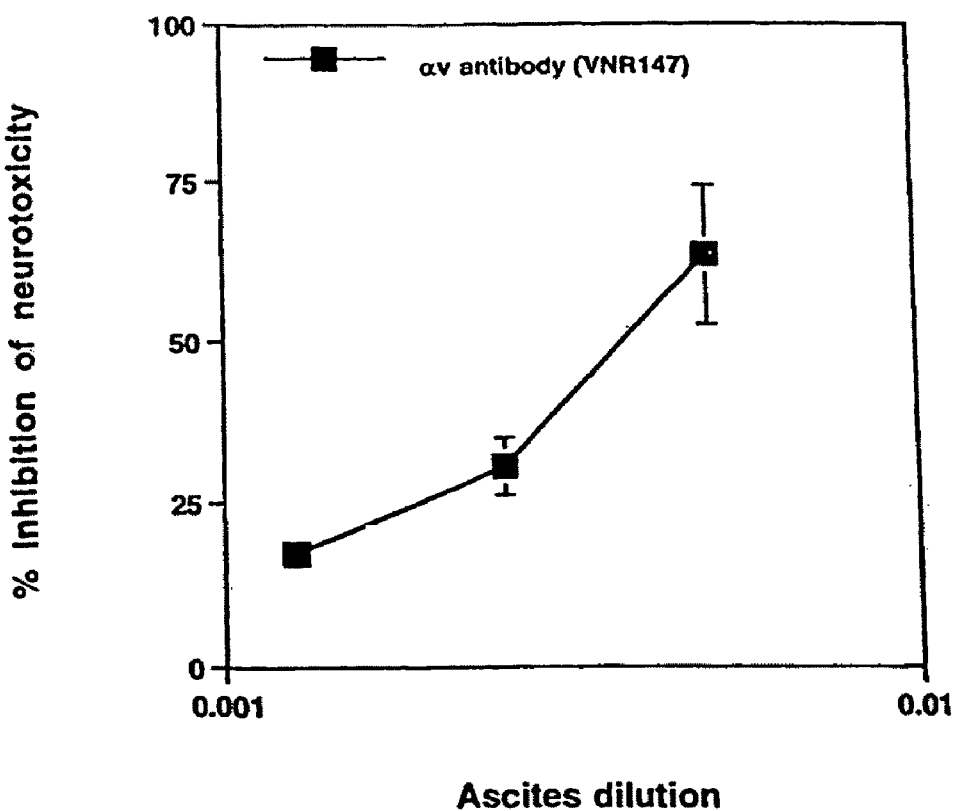

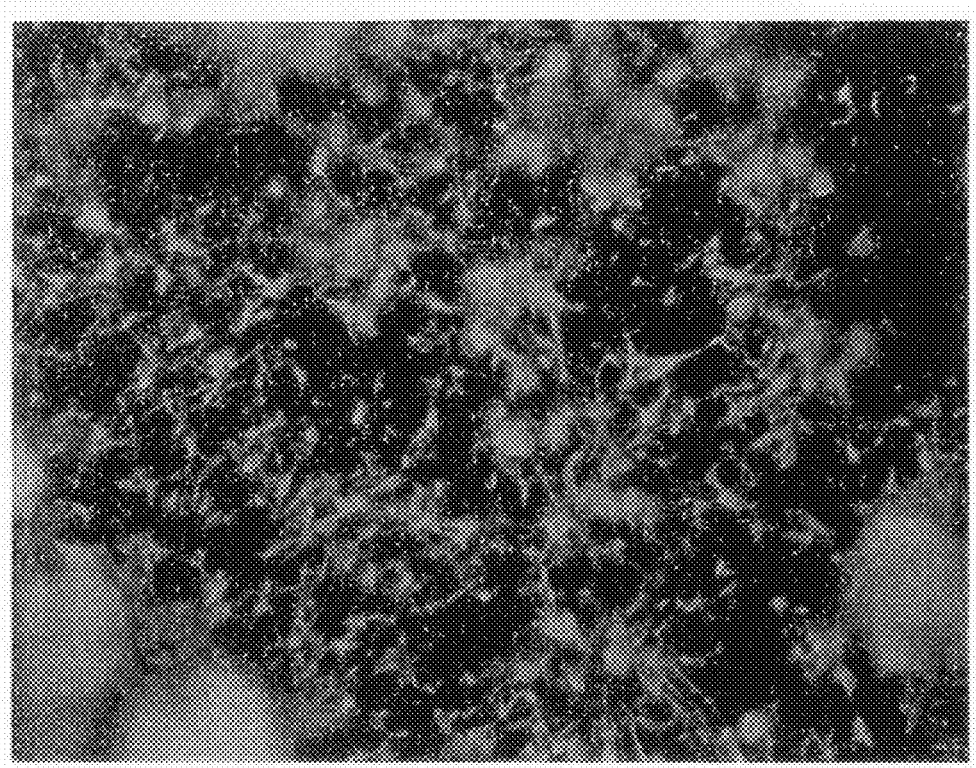
FIG. 5A
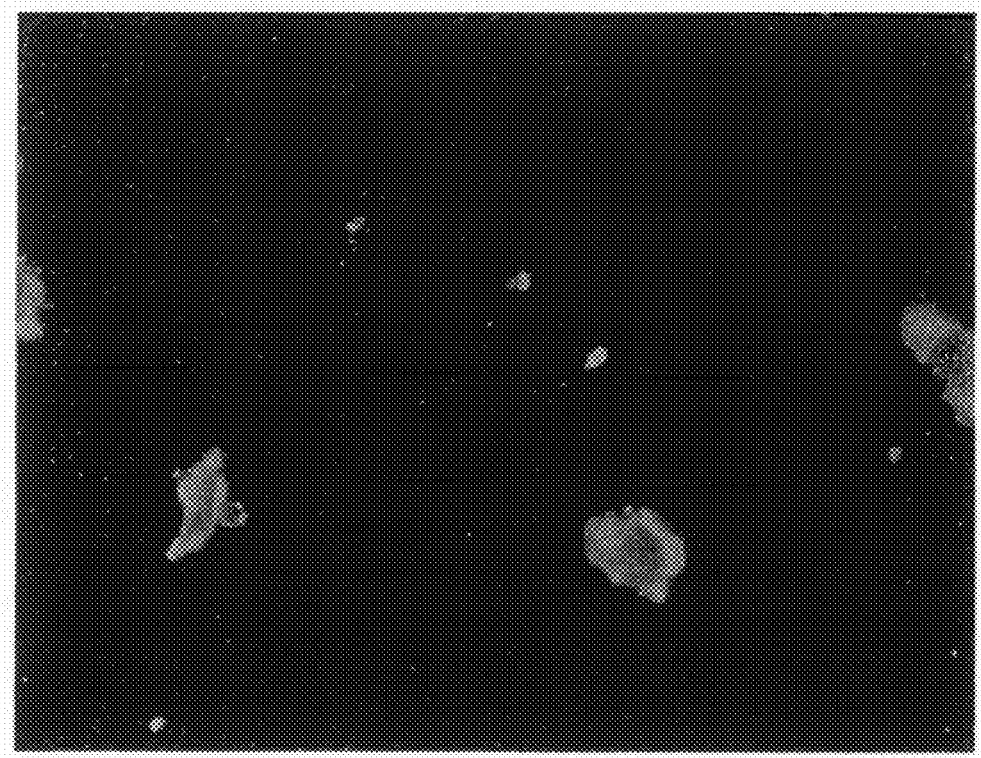

SEQUENCE LISTING

```
<160> NUMBER OF SEQ ID NOS: 5

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

```
Gly Leu Met Val Gly Gly Val Val Ile Ala
        35                  40

<210> SEQ ID NO 2
<211> LENGTH: 43
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 3
<211> LENGTH: 41
<212> TYPE: PRT
<213> ORGANISM: homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile
        35                  40

<210> SEQ ID NO 4
<211> LENGTH: 40
<212> TYPE: PRT
<213> ORGANISM: homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 5
<211> LENGTH: 39
<212> TYPE: PRT
<213> ORGANISM: homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35
```

METHODS OF INHIBITING AMYLOID TOXICITY

CROSS-REFERENCE TO RELATED APPLICATIONS

This application is a divisional application of U.S. patent application Ser. No. 10/190,548 filed on Jul. 9, 2002 and claims priority under 35 U.S.C. §119(e) to U.S. Provisional Application Ser. No. 60/341,772, filed Dec. 17, 2001 and U.S. Provisional Application Ser. No. 60/304,315 filed Jul. 9, 2001, each of which is incorporated by reference herein in its entirety.

Amyloidogenic proteins are involved in the pathology of multiple disease states. Diseases resulting from abnormal deposition of amyloidogenic proteins include, but are not limited to, Alzheimer's disease, type II diabetes, Parkinson's disease, diseases caused all or in part by prions (such as Creutzfeldt-Jakob disease, scrapie, and bovine spongiform encephalopathy), and amyloidoses, including both hereditary amyloidoses and systemic amyloidoses.

Alzheimer's disease (AD) is a progressive neurodegenerative disease resulting in senile dementia that afflicts four million people in the United States alone (see generally Sloe, *TINS*, 16:403-409 (1993); Hardy et al., WO 92/13069; Sloe, *J. Neuropathol. Exp. Neurol.*, 53:438-447 (1994); Duff et al., *Nature*, 373:476-477 (1995); Games et al., *Nature*, 373:523 (1995). Broadly speaking, the disease falls into two categories: late onset, which occurs in old age (65+ years); and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, senile plaques and neurofibrillary tangles. Neurofibrillary tangles are intracellular deposits of microtubule associated tau protein consisting of two filaments twisted about each other in pairs. Senile plaques are areas of disorganized neuropil up to 150 microns across (visible by microscopic analysis of sections of brain tissue) and have extracellular amyloid deposits at the center. The principal component of such plaques is Aβ peptide (see Forsyth *Phys. Ther.*, 78:1325-1331 (1998)). Additional proteins found in the plaques include laminin as described by Murtomaki et al., *J. Neurosci. Res.*, 32:261-273 (1992), apoE, acetylcholinesterase, and heparin sulfate proteoglycans, as described by Yan et al., *Biochim. Biophys. Acta*, 1502:145-57 (2000). Aβ peptide is an internal fragment of 39-43 amino acids of a precursor protein termed amyloid precursor protein (APP). Several mutations within the APP protein have been correlated with the presence of Alzheimer's disease (Goate et al., *Nature*, 349:704-06 (1991) (valine$^{717}$ to isoleucine); Harlin et al., *Nature*, 353:844-46 (1991) (valine$^{717}$ to glycine); Murrell et al., *Science*, 254:97-99 (1991) (valine$^{717}$ to phenylalanine); Mullan et al., *Nature Genet.*, 1:345-47 (1992) (a double mutation changing lysine$^{595}$-methionine$^{596}$ to asparagine$^{595}$leucine$^{596}$). Such mutations are thought to cause Alzheimer's disease by increased or altered processing of APP to Aβ, particularly processing of APP to increased amounts of the long form of Aβ (i.e., A1-42 and A1-43). Mutations in other genes, such as the presenilin genes PS1 and PS2, are thought to indirectly affect processing of APP to generate increased amounts of long form Aβ (Hardy, *TINS*, 20:154 (1997)). These observations indicate that Aβ, and particularly its long form, is a causative element in Alzheimer's disease (Velez-Pardo et al., *Gen. Pharm.*, 31(5):675-81 (1998)).

Almost all individuals with Down's syndrome, who have an extra copy of chromosome 21, show neuropathological changes similar to those seen in Alzheimer's disease, if they survive into their 40s. This has been attributed to excess production of beta-amyloid protein, which is encoded by the APP gene on chromosome 21.

Several proteins have been investigated for possible interactions with Aβ. These include the receptor for advanced glycation endproducts, RAGE (see Yan et al., *Nature*, 382:685-91 (1996)), the scavenger receptor (Khoury et al., *Nature*, 382:716-719 (1996); and Paresce et al., *Neuron* 17:553-65 (1996)), the endoplasmic reticulum-associated amyloid-beta biding protein (ERAB) (Yan et al., *Nature*, 389:689-695 (1997)), α4 or α7 nicotinic acetylcholine receptor (Wang et al., *J. Neurochem.*, 75:1155-1161 (2000) and Wang et al., *J. Biol. Chem.*, 275:5626-5632 (2000)), and the low affinity p75 NGF receptor (see Yaar et al., *J. Clin. Invest.*, 100:2333-2340 (1997)). Additionally, Aβ has been reported to mediate adhesion of cells in a β1-integrin subunit dependent manner when coated onto plates by Ghiso et al., *Biochem. J.*, 288:1053-59 (1992); and Matter et al., *J. Cell Bio.*, 141:1019-1030 (1998).

In view of the number of different molecules of various functions that may interact with Aβ, the mechanism by which Aβ may mediate neurodegeneration remains unclear. The existence and nature of other cellular proteins that may have roles in the process is also unclear.

Islet amyloid has been recognized as a pathological entity in type II diabetes since the turn of the century. It has as its unique component the islet β-cell peptide, islet amyloid polypeptide (IAPP) or amylin, which is co-secreted with insulin. In addition to this unique component, islet amyloid contains other proteins, such as apolipoprotein E and the heparin sulfate proteoglycan perlecan, which are typically observed in other forms of generalized and localized amyloid. Islet amyloid is observed at pathological examination in the vast majority of individuals with type II diabetes but is rarely observed in humans without disturbances of glucose metabolism. In contrast to IAPP from rodents, human IAPP has been shown to form amyloid fibrils in vitro. Because all human subjects produce and secrete the amyloidogenic form of IAPP, yet not all develop islet amyloid, some other factors are likely to be involved in islet amyloid formation. One hypothesis is that an alteration in β-cell function resulting in a change in the production, processing, and/or secretion of IAPP is involved in the initial formation of islet amyloid fibrils in human diabetes. This formation of amyloid fibrils then allows the progressive accumulation of IAPP-containing fibrils. The eventual replacement of β-cell mass by amyloid contributes to the development of hyperglycemia.

One factor that may be involved in producing the changes in the β-cell that result in the initiation of amyloid formation is the increased consumption of dietary fat. Dietary fat is known to alter islet β-cell peptide production, processing, and secretion, and studies in transgenic mice expressing human IAPP support the operation of this mechanism. Further investigation using this and other models should provide insight into the mechanisms involved in islet amyloidogenesis and allow the development of therapeutic agents that inhibit or reverse amyloid fibril formation, with the goal being to preserve β-cell function and improve glucose control in type II diabetes. *Diabetes*, 48:241-253 (1999).

The transmissible spongiform encephalopathies, or prion diseases, constitute a group of transmissible, rapidly progressive, invariably fatal neurodegenerative diseases that can manifest as acquired, hereditary or idiopathic ("sporadic") diseases. They include Creutzfeldt-Jakob disease in humans, as well as scrapie and bovine spongiform encephalopathy (BSE) in animals, and are characterized by a long incubation period that may last up to decades after experimental or accidental transmission. The classic pathological features of prion diseases include spongiform change, gliosis, and neuronal loss. In contrast to what is typically seen in infectious diseases caused by viruses, prion diseases lack a significant inflammatory response (Prusiner, *Arch. Neurol.,* 50:1129-1153 (1953), Prusiner, *Proc. Natl. Acad. Sci. U.S.A.,* 95:13363-13383 (1998).

Prion diseases have received considerable scientific attention due to the unique properties of the transmissible agent, the "prion" (Prusiner, *Science,* 216:136-144 (1982)). The infectious agent is very small and extremely resistant to treatments that destroy nucleic acids and inactivate conventional viruses (id.), but is susceptible to treatments that denature proteins. Attempts to purify the infectious agent yielded fractions highly enriched for a hitherto unknown protein, which has been named prion protein (PrP) (Bolton et al., *Science,* 218:1309-1311 (1982); Prusiner et al, *Cell,* 38:127-134 (1983); Oesch et al., *Cell,* 40:735-746 (1985)). No agent-specific nucleic acid has been found in these preparations (Kellings et al., *J. Gen. Virol.,* 73:1025-1029 (1992); Riesner et al., *Dev. Biol. Stand.,* 80:173-181 (1993)); rather, the prion protein is encoded in the host genome (Oesch et al., *Cell,* 40:735-746 (1985); Chesebro et al., *Nature,* 315:331-333 (1985); Basler et al., *Cell,* 46:417-428 (1986)). In the brains of affected individuals, a pathognomonic accumulation of a specific disease-associated isoform of the prion protein, termed $PrP^{Sc}$, is found (FIG. 1). $PrP^{Sc}$ is derived through an ill-defined post-translational process involving conformational changes from the normal cellular isoform of the prion protein ($PrP^{C}$) (Prusiner, *Proc. Natl. Acad. Sci. U.S.A.,* 95:13363-13383 (1998)). $PrP^{C}$ and $PrP^{Sc}$ have the same amino acid sequence (Stahl et al., *Biochemistry,* 32:1991-2002 (1993)), however, they differ in conformation. $PrP^{Sc}$ can be distinguished from $PrP^{C}$ by its high content of β-sheet structures (Pan et al., *Proc. Natl. Acad. Sci. U.S.A.,* 90:10962-10966 (1993)), its tendency to form large aggregates, and its partial resistance to digestion with proteinase K.

Hereditary amyloidoses comprise a clinically and genetically heterogeneous group of autosomal dominant inherited diseases characterized by the deposit of insoluble protein fibrils in the extracellular matrix. These diseases typically present symptoms of polyneuropathy, carpal tunnel syndrome, autonomic insufficiency, cardiomyopathy, and gastrointestinal features, occasionally accompanied by vitreous opacities and renal insufficiency. Other phenotypes are characterized by nephropathy, gastric ulcers, cranial nerve dysfunction, and corneal lattice dystrophy. Rarely, the leptomeningeal or cerebral structures are also involved in the clinical picture. The age at onset is as early as 17 and as late as 78 years. The basic constituents of amyloid fibrils are physiologic proteins that have become amyloidogenic through genetically determined conformation changes. Mutated transthyretin (TTR), formerly termed prealbumin, is the most frequent offender in hereditary amyloidosis. Orthotopic liver transplantation (OLT) stops the progression of the disease, which is otherwise generally fatal, by removing the main production site of the amyloidogenic protein. The indications for OLT and its success depend on the grade of cardiovascular and autonomic dysfunction at the time of surgery, age, comorbidity, and type of mutation. Alternative treatment modalities with drugs stabilizing the native tetrameric conformation of TTR and inhibiting fibril formation are currently being intensively studied.

Systemic amyloidoses are characterized by the extracellular deposit of fibrillary protein aggregations in parenchymal organs; blood vessels; subcutaneous, submucosal, and peritendinous fat; heart; eyes; and meninges. In addition, any part of the peripheral nervous system may be involved, including the nerve trunks, plexuses, and the sensory and autonomic ganglia. In the peripheral nerves, amyloid deposits occur in the epi-, peri-, or endoneurium, usually in a patchy and localized distribution. On light microscopy with conventional stains, amyloid deposits have a homogeneous, eosinophilic appearance. With Congo red staining, they show a characteristic yellow-green birefringence under polarized light.

A variety of proteins are responsible for amyloid formation; in fact, a total of 18 amyloidogenic proteins have been identified in human amyloidoses. Nonhereditary systemic amyloidoses can be caused by immunoglobulin light chains (AL-type, in plasma cell dyscrasias), fragments of serum amyloid A, an acute-phase protein (AA-type, in chronic inflammatory diseases), transthyretin (TTR; in senile systemic amyloidosis), and $β_2$-microglobulin (in patients with uremia and dialysis). Hereditary amyloidoses are due to genetic variants of physiologic proteins, including TTR and, much more rarely, apolipoprotein-A1, lysozyme, fibrinogen, gelsolin, amyloid-β, and cystatin C. TTR, formerly called prealbumin, is a normal tetrameric serum protein that is involved in the transport of serum thyroxine and retinal-binding protein. It is encoded by a single gene on chromosome 18, of which more than 70 autosomal dominantly inherited point mutations occurring at 51 different sites have been described. Among these, substitution of valine by methionine at position 30 (Met30) is by far the most frequent and geographically most widely disseminated.

Parkinson's disease is a progressive neurological disorder marked by tremors, muscle rigidity, and balance and coordination problems. The destruction of brain cells that produce the chemical dopamine underlies these symptoms. These diseased cells are also marked by protein deposits called Lewy bodies. No one knows why the cells die or whether the Lewy bodies help kill them. Mutations in the genes for two proteins, called parkin and α-synuclein, are linked to separate, rare forms of inherited Parkinson's disease. But both parkin and α-synuclein are found in Lewy bodies that build up in the brains of all Parkinson's disease patients.

Recent findings suggest that parkin plays an important role in regulating proteins associated with Lewy bodies in the brain, including α-synuclein and synphilin. Normally, parkin uses yet another protein, called ubiquitin, to "tag" other proteins for destruction. But if something goes wrong in the relationship among these proteins, this could lay the groundwork for the cell death seen in Parkinson's disease. Both parkin and α-synuclein are linked with synphilin-1 in a common pathogenic mechanism involving the ubiquitination of Lewy body-associated proteins. Dawson et al., *Nature Medicine,* 7:1144-1150 (2001). Thus, given its interaction with parkin, problems with α-synuclein may be at the core of both the inherited and common forms of Parkinson's disease. Id.

SUMMARY OF THE INVENTION

The invention provides methods of inhibiting formation of an amyloid deposit. The methods comprise administering an effective dosage of one or more agents that bind to a molecule selected from among:

(1) an integrin subunit selected from among α2, αv, α6, and β1;

(2) an integrin selected from among α2β1, α6β1, and αvβ1; and
(3) laminin,
under conditions such that the one or more agents inhibit the formation of an amyloid deposit.

In some methods, the agent binds to the α2 integrin subunit.

In some methods, the agent binds to the αv integrin subunit.

In some methods, the agent binds to the β1 integrin subunit.

In some methods, the agent binds to the α6 integrin subunit.

In some methods, the agent binds to the integrin α2β1.

In some methods, the agent binds to the integrin αvβ1.

In some methods, the agent binds to the integrin α6β1.

In some methods, the agent binds to laminin.

In some methods, effective dosages of at least two agents that bind to at least two integrin subunits selected from among α2, α6, αv, and β1 are administered.

In some methods, effective dosages of at least three agents that bind to at least three integrin subunits selected from among α2, α6, αv, and β1 are administered.

In some methods, effective dosages of at least four agents that bind to the integrin subunits α2, α6, αv, and β1 are administered.

In some methods, the agent is a peptide comprising an RGD (Arg-Gly-Asp) motif.

In some methods, the agent is a ligand of αvβ1, α6β1, or α2β1 integrins.

In some methods, the agent is fibronectin or superfibronectin (a multimeric form of fibronectin).

In some methods, the agent inhibits adhesion of α2 integrin subunit-expressing cells to collagen.

In some methods, the agent inhibits adhesion of αv integrin subunit-expressing cells to vitronectin or fibronectin.

In some methods, the agent inhibits adhesion of β1 integrin subunit-expressing cells to fibronectin.

In some methods, the agent inhibits adhesion of αv integrin subunit-expressing cells to osteopontin.

In some methods, the agent inhibits adhesion of α6 integrin subunit-expressing cells to osteopontin.

In some methods, the agent is a monoclonal or polyclonal antibody.

In some methods, the antibody recognizes the same epitope as an antibody selected from among 1965, Lia1/2, Gi9, 1950Z, VNR147, and 1980.

In some methods, the antibody is selected from among 1965, Lia1/2, Gi9, 1950Z, VNR147, and 1980.

In some methods, the agent competes for binding to the integrin α2β1 or αvβ1 with an antibody selected from among 1965, Lia1/2, Gi9, 1950Z, VNR147, and 1980.

In some methods, the agent is a human antibody.

In some methods, the agent is a humanized antibody.

In some methods, the antibody is a mouse antibody.

In some methods, the antibody is a polyclonal antibody.

In some methods, the antibody is a monoclonal antibody.

In some methods, the agent is an antibody fragment.

In some methods the agent comprises one or more heavy chains, light chains, F(ab), F(ab)$_2$, F(ab)$_c$, or F(v) of an antibody.

In some methods, the isotype of the antibody is IgG1 or IgG4.

In some methods, the isotype of the antibody is IgG2 or IgG3.

In some methods, the agent is an antibody chain.

In some methods, the antibody comprises two pairs of light and heavy chains.

In some methods, the dosage of antibody is about 0.01 to about 10 mg/kg body weight of the patient.

In some methods, the agent is administered with a carrier as a pharmaceutical composition.

In some methods, the agent is administered intraperitoneally, orally, intranasally, subcutaneously, intrathecally, intramuscularly, topically or intravenously.

The invention further provides methods of inhibiting amyloid toxicity. These methods comprise administering an effective dosage of one or more agents that bind to a molecule selected from among:
(1) an integrin subunit selected from among α2, αv, α6, and β1;
(2) an integrin selected from among α2β1, α6β1, and αvβ1; and
(3) laminin,
under conditions such that the one or more agents inhibit amyloid toxicity.

The invention further provides methods of screening agents for activity in preventing amyloid plaque deposition. These methods comprise contacting a population of cells with an agent, contacting the population with one or more amyloid peptides (e.g., Aβ or amylin), and monitoring formation of an amyloid deposit. A reduction in the rate or extent of amyloid deposit formation indicates that the agent has activity.

In some methods, the population is contacted with the agent before the amyloid peptide.

The invention further provides compositions comprising an agent that binds to a molecule selected from among:
(1) an integrin subunit selected from among α2, α6, αv, and β1;
(2) an integrin selected from among α2β1, α6β1, and αvβ1; and
(3) laminin,
and a pharmaceutically acceptable carrier.

In some compositions, the agent binds to the α2 integrin subunit.

In some compositions, the agent binds to the αv integrin subunit.

In some compositions, the agent binds to the β1 integrin subunit.

In some compositions, the agent binds to the α6 integrin subunit.

In some compositions, the agent binds to the integrin α2β1.

In some compositions, the agent binds to the integrin α6β1.

In some compositions, the agent binds to the subunit αvβ1.

In some compositions, the agent binds to laminin.

Some compositions comprise effective dosages of at least two agents that bind to at least two integrin subunits selected from among α2, α6, αv, and β1.

Some compositions comprise at least three agents that bind to at least three integrin subunits selected from among α2, α6, αv, and β1.

Some compositions comprise at least four agents that bind to the integrin subunits α2, α6, αv, and β1.

In some compositions, the agent is a peptide comprising an RGD (Arg-Gly-Asp) motif.

In some compositions, the agent is a ligand of αvβ1, α6β1, or α2β1.

In some compositions, the agent is fibronectin or superfibronectin (a multimeric form of fibronectin).

In some compositions, the agent inhibits adhesion of α2-expressing cells to collagen.

In some compositions, the agent inhibits adhesion of αv-expressing cells to vitronectin or fibronectin.

In some compositions, the agent inhibits adhesion of β1-expressing cells to fibronectin.

In some compositions, the agent inhibits adhesion of αv-expressing cells to osteopontin.

In some compositions, the agent inhibits adhesion of α6-expressing cells to osteopontin.

In some compositions, the agent is a monoclonal or polyclonal antibody.

In some compositions, the antibody recognizes the same epitope as an antibody selected from among 1965, Lia1/2, Gi9, 1950Z, VNR147, and 1980.

In some compositions, the antibody is selected from among 1965, Lia1/2, Gi9, 1950Z, VNR147, and 1980.

In some compositions, the agent competes for binding to the integrin α2β1 or αvβ1 with an antibody selected from among 1965, Lia1/2, Gi9, 1950Z, VNR147, and 1980.

In some compositions, the agent is a human antibody.

In some compositions, the agent is a humanized antibody.

In some compositions, the antibody is a mouse antibody.

In some compositions, the antibody is a polyclonal antibody.

In some compositions, the antibody is a monoclonal antibody.

In some compositions, the agent is an antibody fragment.

In some compositions, the agent comprises one or more heavy chains, light chains, F(ab), F(ab)$_2$, F(ab)$_c$, or F(v) of an antibody.

In some compositions, the isotype of the antibody is IgG1 or IgG4.

In some compositions, the isotype of the antibody is IgG2 or IgG3.

In some compositions, the agent is an antibody chain.

In some compositions, the antibody comprises two pairs of light and heavy chains.

In some compositions, the dosage of antibody is about 0.01 to about 10 mg/kg body weight of the patient.

In some compositions, the agent is administered with a carrier as a pharmaceutical composition.

Some compositions are formulated for intraperitoneal, oral, intranasal, subcutaneous, intramuscular, intrathecal, topical or intravenous administration.

The invention further provides methods of preventing or treating an amyloidogenic disease in a patient, comprising administering to the patient an effective dosage of one or more agents that bind to a molecule selected from among:

(1) an integrin subunit selected from among α2, α6, αv, and β1;

(2) an integrin selected from among α2β1, α6β1, and αvβ1; and (3) laminin.

In some methods, the agent binds to the α2 integrin subunit.

In some methods, the agent binds to the αv integrin subunit.

In some methods, the agent binds to the β1 integrin subunit.

In some methods, the agent binds to the α6 integrin subunit.

In some methods, the agent binds to the integrin α2β1.

In some methods, the agent binds to the integrin αvβ1.

In some methods, the agent binds to the integrin α6β1.

In some methods, the agent binds to laminin.

In some methods, effective dosages of at least two agents that bind to at least two integrin subunits selected from among α2, α6, αv, and β1 are administered.

In some methods, effective dosages of at least three agents that bind to at least three integrin subunits selected from among α2, α6, αv, and β1 are administered.

In some methods, effective dosages of at least four agents that bind to the integrin subunits α2, α6, αv, and β1 are administered.

In some methods, the agent is a peptide comprising an RGD (Arg-Gly-Asp) motif.

In some methods, the agent is a ligand of αvβ1, α6β1, or α2β1 integrins.

In some methods, the agent is fibronectin or superfibronectin (a multimeric form of fibronectin).

In some methods, the agent inhibits adhesion of α2 integrin subunit-expressing cells to collagen.

In some methods, the agent inhibits adhesion of αv integrin subunit-expressing cells to vitronectin or fibronectin.

In some methods, the agent inhibits adhesion of β1 integrin subunit-expressing cells to fibronectin.

In some methods, the agent inhibits adhesion of αv integrin subunit-expressing cells to osteopontin.

In some methods, the agent inhibits adhesion of α6 integrin subunit-expressing cells to osteopontin.

In some methods, the agent is a monoclonal or polyclonal antibody.

In some methods, the antibody recognizes the same epitope as an antibody selected from among 1965, Lia1/2, Gi9, 1950Z, VNR147, and 1980.

In some methods, the antibody is selected from among 1965, Lia1/2, Gi9, 1950Z, VNR147, and 1980.

In some methods, the agent competes for binding to the integrin α2β1 or αvβ1 with an antibody selected from among 1965, Lia1/2, Gi9, 1950Z, VNR147, and 1980.

In some methods, the agent is a human antibody.

In some methods, the agent is a humanized antibody.

In some methods, the antibody is a mouse antibody.

In some methods, the antibody is a polyclonal antibody.

In some methods, the antibody is a monoclonal antibody.

In some methods, the agent is an antibody fragment.

In some methods the agent comprises one or more heavy chains, light chains, F(ab), F(ab)$_2$, F(ab)$_c$, or F(v) of an antibody.

In some methods, the isotype of the antibody is IgG1 or IgG4.

In some methods, the isotype of the antibody is IgG2 or IgG3.

In some methods, the agent is an antibody chain.

In some methods, the antibody comprises two pairs of light and heavy chains.

In some methods, the dosage of antibody is about 0.01 to about 10 mg/kg body weight of the patient.

In some methods, the agent is administered with a carrier as a pharmaceutical composition.

In some methods, the agent is administered intraperitoneally, orally, intranasally, subcutaneously, intrathecally, intramuscularly, topically or intravenously.

In some methods, the agent is a polypeptide, and the agent is administered by administering a polynucleotide encoding the polypeptide to the patient, wherein the polynucleotide is expressed in the patient.

In some methods, the patient is monitored for the amount of administered agent in the blood of the patient.

In some methods, the disease is Alzheimer's disease.

In some methods, the disease is type II diabetes.

In some methods, the disease is Parkinson's disease.

In some methods, the disease is caused all or in part by prion infection.

In some methods, the disease is an amyloidosis such as a hereditary or systemic amyloidosis.

In some methods, the disease is Down's syndrome.

In some methods, the patient is human.

In some methods, the patient is asymptomatic.

In some methods, the patient is under 50, in others, the patient is 50 or older.

In some methods, the patient has inherited risk factors indicating susceptibility to Alzheimer's disease.

The invention further provides methods of preventing or treating an amyloidogenic disease in a patient comprising administering to the patient an effective dosage of an agent that inhibits formation of an extracellular meshwork of amyloid proteins such as Aβ or amylin.

The invention further provides methods of preventing or treating an amyloidogenic disease in a patient comprising administering to the patient an effective dosage of an agent that suppresses expression of a gene selected from among:

1) a gene encoding an integrin subunit selected from among α2, αv, α6, and β1; and 2) a gene encoding laminin.

In some methods, the agent is an antisense nucleic acid.

In some methods, the agent is a zinc finger protein.

In some methods, the agent suppresses expression of a gene encoding the α2 integrin subunit.

In some methods, the agent suppresses expression of a gene encoding the αv integrin subunit.

In some methods, the agent suppresses expression of a gene encoding the β1 integrin subunit.

In some methods, the agent suppresses expression of a gene encoding the α6 integrin subunit.

BRIEF DESCRIPTION OF THE FIGURES

FIG. 1 illustrates the Aβ meshwork in human cortical cultures (HCC) (top) or polyethyleneimine (PEI) (bottom) coated plates.

FIG. 2 illustrates the effects of β1 integrin subunit on both Aβ meshwork formation and neurotoxicity in HCC. FIG. 2B illustrates 72 hour Aβ meshwork formation in HCC in the absence (top) or presence (bottom) of the anti-β1 antibody, 1965.

FIG. 3C illustrates the neurotoxicity in HCC preincubated with β1 integrin subunit blocking antibodies.

FIG. 5 illustrates the effects of anti-laminin antibodies in inhibiting Aβ meshwork formation and neurotoxicity. FIG. 5A illustrates 72 hour Aβ meshwork formation in HCC preincubated in the absence (top) or presence of anti-laminin antibody (bottom).

FIG. 6 illustrates activation of the Aβ signaling pathway in HCC.

DEFINITIONS

Figure 2A:
FIG. 2A illustrates β1 integrin subunit expression in HCC.

Therapeutic agents of the invention are typically substantially purified from undesired contaminants. This means that an agent is typically at least about 50% w/w (weight/weight) purity, as well as being substantially free from interfering proteins and contaminants. Sometimes the agents are at least about 60%, 70%, 80%, 90%, or 95% w/w purity. Using conventional protein purification techniques, homogenous peptides of at least 99% w/w can also be obtained.

Specific binding between two entities means an affinity of at least $10^6$, $10^7$, $10^8$, $10^9$, or $10^{10}$ M$^{-1}$. In one embodiment, affinities are greater than about $10^8$ M$^{-1}$.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab', F(ab')$_2$, F(ab)c, and Fv. Fragments may be produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments (See, e.g., Songsivilai and Lachmann, *Clin. Exp. Immunol.*, 79:315-321 (1990); Kostelny et al., *J. Immunol.*, 148:1547-53 (1992)).

APP$^{695}$, APP$^{751}$, and APP$^{770}$ refer, respectively, to the 695, 751, and 770 amino acid residue long polypeptides encoded by the human APP gene. See Kang et al., *Nature,* 325:733-36 (1987); Ponte et al., *Nature,* 331:525-27 (1988); and Kitaguchi et al., *Nature,* 331:530-32 (1988). Amino acids within the human amyloid precursor protein (APP) are assigned numbers according to the sequence of the APP$^{770}$ isoform. Terms such as Aβ39, Aβ40, Aβ41, Aβ42, and Aβ43 refer to an Aβ peptide containing amino acid residues 1-39, 1-40, 1-41, 1-42, and 1-43. Aβ42 has the sequence (SEQ ID NO:1):

H2N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH. Aβ41 (SEQ ID NO:3), Aβ40 (SEQ ID NO:4), and Aβ39 (SEQ ID NO:5) differ from Aβ42 (SEQ ID NO:1) by the omission of Ala, Ala-Ile, and Ala-Ile-Val, respectively, from the C-terminal end. Aβ43 (SEQ ID NO:2) differs from Aβ42 (SEQ ID NO:1) by the presence of a threonine residue at the C-terminus.

"Amylin" refers to the protein known commonly in the art or to a peptide or polypeptide or fragment thereof, or to a precursor protein or polymer of the protein, peptide or polypeptide. The term encompasses islet amyloid polypeptide. A description of amylin may be found in the art in such places as Cooper et al., *Proc. Natl. Acad. Sci. U.S.A.*, 85:7763 (1988) and Leighton et al., *Nature*, 335:632 (1988).

The term "amyloid peptide or protein" refers to the family of peptides and proteins that form amyloid-like deposits, including amylin and Aβ.

The phrase "amyloid or amyloid-like deposits" includes amyloid fibrils as well as other amyloid or amyloid-like deposits, fibrillar or nonfibrillar in structure, which are recognized in the art as being amyloid or amyloid-like, such as deposits in senile amyloidosis (e.g., Aβ), prion-related encephalopathies (e.g., PrP), and in the kidney or pancreas of diabetic patients (e.g., amylin), etc. On light microscopy with conventional stains, such deposits have a homogeneous, eosinophilic appearance. With Congo red staining, they show a characteristic yellow-green birefringence under polarized light. The term also includes pre-amyloid deposits, which unlike amyloid deposits, do not stain with Congo Red.

The term "amyloidogenic disease" is intended to encompass a disease characterized by unwanted deposition of a protein or peptide. The term specifically encompasses diseases characterized by unwanted deposition of amyloid peptides such as occurs in type II diabetes (e.g., amylin), Alzheimer's disease (e.g., Aβ), multiple myeloma, and rheumatoid arthritis, as described by Kahn et al., *Diabetes*, 48:241-253 (1999); and Johnson et al., *Laboratory Investigation*, 66(5): 522-535 (1992). The term also specifically encompasses diseases characterized by unwanted deposition of amyloidogenic proteins such as Parkinson's disease or hereditary or systemic amyloidoses as described by Hund et al., *Neurology*, 56:431-435 (2001) including those mediated by transthyretin (TTR) deposition. Moreover, the term includes diseases caused all or in part by infection with a prion such as Creutzfeldt-Jakob disease. Such prion mediated diseases are characterized by accumulation of a prion protein as described by Giese et al., *Curr. Topics Microbiology and Immunology*, 253:203-217 (2001). In short, the term is meant to include all diseases wherein the pathology is mediated by unwanted protein or peptide deposits that adversely affect the health and well-being of surrounding cells.

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols, in Methods in Molecular Biology*, Vol. 66, Glenn E. Morris, Ed. (1996). Antibodies that recognize the same or overlapping epitopes can be identified in a simple immunoassay showing the ability of one antibody to block the binding of another antibody to a target antigen.

The term "naked polynucleotide" or "naked DNA" refers to a polynucleotide not complexed with colloidal materials, e.g., proteins. Naked polynucleotides are sometimes cloned in a plasmid vector.

The term "patient" includes human and other mammalian subjects that receive either prophylactic or therapeutic treatment.

Neuronal cells can be exposed to Aβ peptide as a result of the natural processing of APP to Aβ that occurs in vivo, or as a result of contacting the neuronal cells with a preparation of Aβ in an in vitro assay. Exposure to Aβ peptide can occur before, after, or at the same time as exposure to drugs.

Amyloid deposits of Aβ peptide refer to aggregates of the Aβ peptides, possibly including fibrils, that form on and around cortical cells in vitro, such as shown in FIG. 1A, or in vivo.

Unless otherwise apparent from the context, reference to fibronectin includes superfibronectin.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology*, 9:242-53 (1983)); solid phase direct biotin-avidin EIA (see Kirkland et al., *J. Immunol.*, 137:3614-19 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., *Molec. Immunol.*, 25(1):7-15 (1988)); solid phase direct biotin-avidin EIA (Cheung et al., *Virology*, 176:546-52 (1990)); and direct labeled RIA (Moldenhauer et al., *Scand. J. Immunol.*, 32:77-82 (1990)). Typically, such an assay involves the use of purified antigen bound to a solid surface or cells bearing either an unlabelled test immunoglobulin or a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

Compositions or methods "comprising" one or more recited elements may include other elements not specifically recited. For example, a composition that comprises antibody may contain the antibody alone or in combination with other ingredients.

DESCRIPTION OF THE INVENTION

A. General

The invention provides methods of inhibiting or preventing formation of extracellular meshworks of amyloid proteins, such as amylin and Aβ peptide, methods for mediating the toxic effects of such proteins, and agents for use in the methods. The methods can be used to treat or prevent Alzheimer's disease, type II diabetes, Parkinson's disease, systemic and hereditary amyloidoses, as well as diseases caused all or in part by prion infection. Agents effective for use in these methods include antibodies and other agents that bind to an integrin subunit such as β1, α2, α6, or αv. These subunits associate as heterodimeric receptors to form integrins, e.g., α2β1, α6β1, and αvβ1. The above agents can be used individually or in combinations to inhibit interaction between integrins and the Aβ peptide. Use of an agent or agents that inhibit interactions between both αvβ1 and α2β1 integrins and Aβ is preferred. Fibronectin, a ligand of integrin, αvβ1, can also be used as an agent, as can antibodies to laminin, a ligand of αvβ1 in the above methods.

The invention is premised, in part, on the observation that antibodies to α2, αv, α6 and β1 integrin subunits inhibit formation of extracellular meshworks of amyloid proteins, such as amylin and Aβ peptide. Thereby, such antibodies inhibit the toxicity of amyloid proteins. The αvβ1 ligand, fibronectin, also inhibits meshwork formation. The α2β1 ligand, laminin, does not inhibit meshwork formation but antibodies to laminin do inhibit meshwork formation and toxicity.

B. Integrins

Integrins are a superfamily of cell surface adhesion heterodimeric transmembrane receptors, which control the attachment of cells both to the extracellular matrix and to other cells. Adhesion provides anchorages and signals for growth, migration, and differentiation. Integrins are formed by the association of one of about fifteen known alpha chains with one of about eight known beta chains. All human cells but erythrocytes express one or more integrins.

Integrin subunits α2, αv, α6 and β1 are all well known. Exemplary human sequences are retrievable from GenBank accession numbers AF062039, M14648, X59512 and X07979, respectively. Unless otherwise indicated, reference to α2, αv, α6, β1 includes these exemplary sequences, allelic variants thereof, and cognate variants from other species. Induced variants of these sequences, having sufficient sequence identity to the natural sequence to compete with the natural sequence for specific binding to a ligand of the natural sequence, can also be used in some methods. Integrins containing αv and one of the β subunits β1, β3, β5, β6 or β8 recognize ligands bearing an RGD motif, but the binding specificity varies depending on which β subunit is present. αvβ1 is known to recognize vitronectin (GenBank accession number X03168), fibronectin (GenBank accession number M26179) and osteopontin (GenBank accession number J04765). Fibronectin is a large multidomain glycoprotein found in connective tissue, on cell surfaces, and in plasma and other body fluids. Fibronectin acts with a variety of macromolecules, including components of the cytoskeleton and the extracellular matrix, circulating components involved in the blood clotting response, fibrinolytic, acute phase and complement systems, and with cell-surface receptors on a variety of cells including fibroblasts, neurons, phagocytes, and bacteria.

Integrins containing α2 and β1 subunits are known as VLA-2 (very late activation antigen 2), GPIa-IIa (glycoprotein Ia-IIa on platelets), and ECMRII (extracellular matrix receptor II). The α2β1 integrins bind collagen-I to VI, laminin and possibly fibronectin. The receptor is expressed on B and T lymphocytes, platelets, fibroblasts, endothelial cells, and melanoma cells, and specifically recognizes collagen and laminins as ligands. Laminins are large, multi domain proteins with a common structural organization. Laminin molecules have alpha, beta, and gamma chain subunits joined together though a coiled coil domain. At least five alpha chains, two beta chains, and three gamma chains are known, and at least twelve laminins having different combinations of these chains have been reported (WO 00/66730). Laminin is found in extracellular matrices including plaques in Alzheimer's disease (Murtomaki, et al., *J. Neuro. Res.*, 32:261-73 (1992); Bronfinan, et al., *Int. J. Exp. Clin. Invest.*, 5:16-23 (1997); and Castillo, et al., *J. Neuro. Res.*, 62:451-62 (2000)). Collagen is the most abundant protein in mammals and is the main fibrous component of skin, bone, tendon, cartilage, and teeth. There are more than 23 known collagen genes (Adams et al., *Am. J. Respir. Cell. Molec. Biol.*, 1:161-168 (1989)).

The α6/β1 integrin is expressed on platelets, lymphocytes, monocytes, thymocytes, and epithelial cells, on which it functions as a laminin receptor for laminin-1, laminin-2, and laminin-4 in vivo. It is also a receptor for laminin-5, but not in vivo. For laminin-1, the binding site has been localized in the E8 domain of this extracellular matrix molecule. This receptor is also known as very late activation antigen 6 (VLA-6) and glycoprotein Ic-IIa (GPIc-IIa on platelets).

Integrins are an example of a larger class of proteins known as adhesion proteins that also includes selectins and immunoglobulin (Ig) superfamily members (see Springer, *Nature*, 346:425 (1990); Osborn, *Cell*, 62:3 (1990); Hynes, *Cell*, 69:11 (1992), which are incorporated by reference in their entirety for all purposes). Antibodies and other agents that bind to adhesion proteins or their ligands, and/or block interaction between the two, can be screened for activity in preventing or inhibiting the accumulation of Aβ deposits in the methods of screening described below. Examples of other selectins and their ligands suitable for screening by the methods described below include integrins α2β5, αvβ5, α6β5, α2β6, αvβ6, and α6β6. Other ligands besides α2β1 that bind to collagen may also be screened.

C. Agents

Therapeutic agents of the invention include antibodies that specifically bind to α2, αv, α6, and β1 integrin subunits. Binding can be assessed either with isolated integrin subunits or fragments thereof, optionally immobilized to a solid phase, or with integrin subunits expressed on the surface of cells. Often, binding is analyzed using cells expressing a heterodimeric integrin. For example, if an agent binds to cells expressing α2β1 as the only integrin, then it can be concluded that the agent binds to α2 or β1 or to α2β1 without binding to either subunit alone. These possibilities can be distinguished by testing binding of the same agent to cells bearing a different heterodimeric integrin. For example, if the same agent specifically binds to cells bearing αvβ1 as the only integrin present, then it is likely that the agent is binding to the β1 subunit. A variety of antibodies to integrin and integrin subunits are commercially available, some of which are described in the Examples.

Monoclonal or polyclonal antibodies can be used in the methods of the invention. Preferred antibodies block interaction of these integrin subunits with one or more of their natural ligands. That is, blocking antibodies to αvβ1 block interaction of this integrin with fibronectin, osteopontin and/or vitronectin. For example, the 14D9.F8 antibody described by WO 99/37683 blocks binding of αv to fibronectin. Blocking antibodies to α2β1 block interaction of this integrin with collagen or laminin. The capacity of an antibody or other agent to block can be recognized by a simple assay in which cells expressing an integrin are tested for adhesion to a plate coated with ligand in the presence or absence of antibody (or other agent). A reduction of at least about 30%, 40%, 50%, 60%, 70%, 80%, 90%, or 100% of the amount of cells binding to the plate identifies a blocking antibody (or other agent) when the antibody is present in molar excess relative to the integrin. Further analyses of the blocking capacity of the agent to other combinations of integrin subunits can pinpoint which subunit of a heterodimeric integrin is being blocked. Binding specificity of an antibody or other agent can also be determined by a competition assay in which a test antibody competes with a reference antibody known to have the desired epitope specificity for binding to an integrin subunit or cells bearing the same. If the test and reference antibodies compete, then they bind to the same epitope or epitopes sufficiently proximal that binding of one antibody interferes with binding of the other. In some embodiments, transfected cells express a single type of integrin.

Some antibodies for use in the invention bind to only one type of integrin subunit. Some antibodies specifically bind to two or more integrin subunits. Some antibodies bind only when the subunits of an integrin are associated as a heterodimeric integrin. For example, some antibodies bind to α2β1 without binding to either α2 or β1 alone. Some antibodies bind to αvβ1 without binding to either αv or β1 alone. Some antibodies bind to subunits both in free form and when the subunit is a component of a heterodimeric integrin. Peptides and small molecules that have the same binding specificity of the above antibodies can also be used.

Other therapeutic agents for use in the invention include fibrinogen, osteopontin, vitronectin, fragments thereof, and other natural or synthetic peptides containing an RGD peptide motif that competes with fibrinogen or vitronectin for binding to αvβ1. Small molecule mimetics that compete with fibrinogen, vitronectin, or osteopontin for binding to αvβ1 can also be used. Other therapeutic agents include antibodies to laminin, and peptides and small molecules with the same binding specificity.

Candidate therapeutic agents can be evaluated by performing one or more of the following screens. Typically, agents are first evaluated for specific binding to an integrin subunit, α2, αv, α6, or β1, and/or a heterodimeric integrin α2β1, αvβ1, α6β1, or laminin. Suitable agents typically bind with specific affinities of at least $10^7$, $10^8$, $10^9$ or $10^{10}$ M$^{-1}$.

Thereafter, candidates are optionally evaluated for a particular epitope specificity. This can be determined by a competition assay with a reference agent, by a functional plate blocking assay as described above, or by an epitope mapping experiment in which an antibody or other agent is evaluated by Western blotting or ELISA for its capacity to bind a series of deletion mutants of an antigen. The smallest fragment to show specific binding to the antibody or other agent defines the epitope of the antibody or other agent. Alternatively, or additionally, candidate agents are evaluated for the capacity to inhibit formation of extracellular meshworks of amyloid peptides. Suitable agents typically reduce toxicity resulting from treatment with amyloid peptides, such as amylin or Aβ, in the presence of an agent relative to a control by at least about 10%, 20%, 30%, 40%, 50%, 60%, 70%, 80%, 90%, or 100% or more.

Candidate compounds can also be tested for prophylactic and therapeutic efficacy in transgenic animals predisposed to an amyloidogenic disease. Such animals include, for example, mice bearing a 717 mutation of APP described by Games et al., supra, and mice bearing a 670/671 Swedish mutation of APP such as described by McConlogue et al., U.S. Pat. No. 5,612,486; Hsiao et al., *Science*, 274:99 (1996); Sturchler-Plerrat et al., *Proc. Natl. Acad. Sci. U.S.A.*, 94:13287-92 (1997); and Borchelt et al., *Neuron*, 19:939-45 (1997). Agents showing activity in transgenic mice can then be evaluated in human clinical trials. Exemplary formats for conducting human clinical trials in Alzheimer's patients are described in WO 98/24678, which is incorporated herein by reference.

A. Antibodies
1. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD, and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., Ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3, and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.*, 196:901-17 (1987); Chothia et al., *Nature*, 342:878-83 (1989).

2. Production of Nonhuman Antibodies

The production of nonhuman monoclonal antibodies, e.g., murine, guinea pig, primate, rabbit, or rat, can be accomplished by, for example, immunizing the animal with an integrin, subunits thereof, or fragments thereof, or with cells bearing the integrin or a subunit thereof. Laminin can also be used as an immunogen for generating antibodies to laminin. See Harlow & Lane, *Antibodies, A Laboratory Manual* (Cold Spring Harbor Press, NY, 1988, incorporated herein by reference for all purposes). Such an immunogen can be obtained from a natural source, by peptide synthesis, or by recombinant expression. Optionally, the immunogen can be administered fused or otherwise complexed with a carrier protein, as described below. Optionally, the immunogen can be administered with an adjuvant. Several types of adjuvant can be used as described below. Complete Freund's adjuvant followed by incomplete adjuvant is preferred for immunization of laboratory animals. Rabbits, goats, sheep, or guinea pigs are typically used for making polyclonal antibodies. Mice are typically used for making monoclonal antibodies. Antibodies are screened for specific binding to the intended integrin or subunit thereof, or other antigen such as laminin. Antibodies can also be screened for the capacity to block binding of an integrin to its ligand as described above. Other screening procedures described above can also be conducted.

3. Chimeric and Humanized Antibodies

Chimeric and humanized antibodies may have the same or similar binding specificity and affinity as a mouse or other nonhuman antibody that provides the starting material for construction of a chimeric or humanized antibody. Some chimeric or humanized antibodies have affinities within a factor of 2-fold, 5-fold or 10-fold that of a mouse. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1, IgG2, IgG3, or IgG4. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a nonhuman antibody such as a mouse-antibody, (referred to as the donor immunoglobulin). See Queen et al., *Proc. Nat. Acad. Sci. U.S.A.*, 86:10029-33 (1989) and WO 90/07861, U.S. Pat. No. 5,693,762, U.S. Pat. No. 5,693,761, U.S. Pat. No. 5,585,089, U.S. Pat. No. 5,530,101, and Winter, U.S. Pat. No. 5,225,539 (each of which are incorporated herein by reference in their entirety for all purposes). The constant region, if present, is also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g., is within about 6 angstroms of a CDR region), or (4) participates in the VL-VH interface.

Other candidates for substitution are acceptor human framework amino acids that are unusual for a human immunoglobulin at that position. These amino acids can be substituted with amino acids from the equivalent position of the donor antibody or from the equivalent positions of more typical human immunoglobulins. The variable region frameworks of humanized immunoglobulins usually show at least 85% sequence identity to a human variable region framework sequence or consensus of such sequences.

4. Human Antibodies

Human antibodies against the above integrins or laminin are provided by a variety of techniques described below. Some human antibodies are selected by competitive binding experiments, or otherwise, to have the same epitope specificity as a particular mouse antibody, such as one of the mouse monoclonals described in the Examples. Human antibodies can also be screened for a particular epitope specificity by using only a fragment of an integrin or laminin as the immunogen, and/or by screening antibodies against a collection of deletion mutants of the integrin.

a. Trioma Methodology

The basic approach and an exemplary cell fusion partner, SPAZ-4, for use in this approach have been described by Oestberg et al., *Hybridoma*, 2:361-67 (1983); Oestberg, U.S. Pat. No. 4,634,664; and Engleman et al., U.S. Pat. No. 4,634,666 (each of which is incorporated herein by reference in its entirety for all purposes). The antibody-producing cell lines obtained by this method are called triomas, because they are descended from three cells—two human and one mouse. Initially, a mouse myeloma line is fused with a human B-lymphocyte to obtain a nonantibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes, or bone marrow of a human donor. If antibodies against a specific antigen or epitope are desired, it is preferable to use that antigen or an epitope thereof for immunization. Immunization can be either in vivo or in vitro. For in vivo immunization, B cells are typically isolated from a human immunized with Aβ, a fragment thereof, larger polypeptide containing Aβ or fragment, or an anti-idiotypic antibody to an antibody to A. In some methods, B cells are isolated from the same patient who is ultimately to be administered antibody therapy. For in vitro immunization, B-lymphocytes are typically exposed to antigen for a period of 7-14 days in a medium such as RPMI-1640 (see Engleman, supra) supplemented with 10% human plasma.

The immunized B-lymphocytes are fused to a xenogeneic hybrid cell such as SPAZ-4 by well known methods. For example, the cells are treated with 40-50% polyethylene glycol of MW 1000-4000, at about 37° C., for about 5-10 min. Cells are separated from the fusion mixture and propagated in medium selective for the desired hybrids (e.g., containing Hypoxanthine+Amethopterin+Thymidine (HAT Media) or Amethopterin+Hypoxanthine (AH Media)). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial, or yeast cell lines.

b. Transgenic Non-Human Mammals

Human antibodies against integrins or laminin can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes non-rearranged sequences of heavy and light chain components. Both the inactivation of endogenous immunoglobulin genes and the introduction of exogenous immunoglobulin genes can be achieved by the targeted homologous recombination, or by introduction of yeast artificial chromosomes (YACs). The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-53 (1994), Fishwild et al., *Nature Biotechnology*, 14, 845-51 (1996), Kucherlapati, WO 91/10741 (1991) (each of which is incorporated by reference in its entirety for all purposes). Transgenic mice are particularly suitable. Anti-integrin or anti-laminin antibodies are obtained by immunizing a transgenic nonhuman mammal, such as described by Lonberg or Kucherlapati, supra, with an integrin or subunit or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using an integrin or laminin as an affinity reagent.

c. Phage Display Methods

A further approach for obtaining human anti-integrin or anti-laminin antibodies is to screen a DNA library from human B cells according to the general protocol outlined by Huse et al., *Science*, 246:1275-81 (1989). As described for trioma methodology, such B cells can be obtained from a human immunized with an integrin, subunits, or fragments thereof, or laminin and fragments thereof. Optionally, such B cells are obtained from a patient who is ultimately to receive antibody treatment. Antibodies binding to an antigen of interest or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743, U.S. Pat. No. 5,565,332, U.S. Pat. No. 5,969,108, U.S. Pat. No. 6,172,197 (each of which is incorporated herein by reference in its entirety for all purposes). Additional methods for selecting and labeling antibodies, or other proteins, that bind to a particular ligand are described by U.S. Pat. No. 5,994,519 and U.S. Pat. No. 6,180,336.

In phage display methods, libraries of phage are produced in which members display different antibodies on their outer surfaces. Antibodies are usually displayed as Fv or Fab fragments. Phage displaying antibodies with a desired specificity are selected by affinity enrichment to an integrin, subunit, or fragment thereof.

In a variation of the phage display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for Aβ (e.g., at least about $10^8$ or at least about $10^9$ $M^{-1}$) is selected. The human heavy chain variable region from this phage then serves as the starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for a desired integrin are selected. These phage display the variable regions of completely human anti-integrin antibodies. These antibodies usually have the same or similar epitope specificity as the murine starting material.

5. Selection of Constant Region

The heavy and light chain variable regions of chimeric, humanized, or human antibodies can be linked to at least a portion of a human constant region. The choice of constant region depends, in part, on whether antibody-dependent complement and/or cellular mediated toxicity is desired. For example, isotypes IgG1 and IgG3 have complement activity and isotypes IgG2 and IgG4 do not. Choice of isotype can also affect passage of the antibody into the brain. Light chain constant regions can be lambda or kappa. Antibodies can be expressed as tetramers containing two light and two heavy chains, as separate heavy chains, light chains, as Fab, Fab', F(ab')$_2$, and Fv, or as single chain antibodies in which heavy and light chain variable domains are linked through a spacer.

6. Expression of Recombinant Antibodies

Chimeric, humanized, and human antibodies are typically produced by recombinant expression. Recombinant polynucleotide constructs typically include an expression control sequence operably linked to the coding sequences of the antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences and for the collection and purification of the crossreacting antibodies.

These expression vectors typically replicate in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*Escherichia coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include the 3-phosphoglycerate kinase promoter and promoters from other glycolytic enzymes. Inducible yeast promoters include, among others, the promoters from alcohol dehydrogenase, isocytochrome C, and the enzymes responsible for maltose and galactose utilization.

Mammalian cells are a preferred host for expressing nucleotide segments encoding immunoglobulins, or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, L cells, and myeloma cell lines. Preferably, the cells are nonhuman. Expression vectors for these cells can include expression control sequences, such as an origin of replication, a promoter, an enhancer (Queen et al., *Immunol. Rev.,* 89:49-68 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.,* 148:1149-54 (1992).

Alternatively, antibody coding sequences can be incorporated in transgenes for introduction into the genome of a transgenic animal and subsequent expression in the milk of the transgenic animal (see, e.g., U.S. Pat. No. 5,741,957, U.S. Pat. No. 5,304,489, U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, and microinjection. For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures known in the art, including HPLC purification, column chromatography, gel electrophoresis, and the like (see generally, Scopes, *Protein Purification* (Springer-Verlag, NY, 1982)).

B. Other Agents

Agents can be naturally occurring or synthetic molecules. Agents to be screened can also be obtained from natural sources, such as, e.g., marine microorganisms, algae, plants, and fungi. For example, U.S. Pat. No. 6,096,707, provides peptides derived from jararhagin, a metalloproteinase from the pit viper *Bothrops jararaca*. These peptides contain the amino acid motif Arg-Lys-Lys (RKK), and decrease the interaction of the human $\alpha 2\beta 1$ integrin with collagen. Alternatively, agents to be screened can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Agents can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, and chimeric molecules.

A variety of methods are available for producing peptide libraries (see, e.g., Lam et al., *Nature,* 354:92, 1991 and WO 92/00091; Geysen et al., *J. Immunol. Meth.,* 102:259 (1987); Houghten et al., *Nature,* 354:84 (1991); WO 92/09300; and Lebl et al., *Int. J. Pept. Prot. Res.,* 41:201 (1993)). Peptide libraries can also be generated by phage display methods. See, e.g., Devlin, WO 91/18980.

Combinatorial libraries can be produced for many types of compounds that can be synthesized in a step-by-step fashion (see e.g., Ellman & Bunin, *J. Amer. Chem. Soc.,* 114:10997, 1992 (benzodiazepine template), WO 95/32184 (oxazolone and aminidine template), WO 95/30642 (dihydrobenzopyran template), and WO 95/35278 (pyrrolidine template)). Libraries of compounds are usually synthesized by solid phase chemistry. However, solution-phase library synthesis can also be useful. Strategies for combinatorial synthesis are described by Dolle & Nelson, *J. Combinatorial Chemistry,* 1:235-282 (1999) (incorporated herein by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth. Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. These methods are particularly amenable for tagging as described in more detail below. The size of libraries generated by such methods can vary from 2 different compounds to $10^6$, or $10^{10}$, or any range there between.

Preparation of Encoded Libraries is Described in a Variety of Publications Including Needels, et al., *Proc. Natl. Acad. Sci. U.S.A.,* 90:10700 (1993); Ni, et al., *J. Med. Chem.,* 39:1601 (1996), WO 95/12608, WO 93/06121, WO 94/08051, WO 95/35503, and WO 95/30642 (each of which is incorporated herein by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both.

Compounds synthesizable by such methods include polypeptides, beta-turn mimetics, polysaccharides, phospholipids, hormones, prostaglandins, steroids, aromatic compounds, heterocyclic compounds, benzodiazepines, oligomeric N-substituted glycines, and oligocarbamates. Prepared combinatorial libraries are also available from commercial sources (e.g., ChemRx, South San Francisco, Calif.).

Combinatorial libraries and other compounds are initially screened for suitability by determining their capacity to bind to $\alpha 2\beta 1$, $\alpha 6\beta 1$, or $\alpha v\beta 1$ integrins, or to laminin. The additional screening procedures described above can also be used.

C. Gene Suppression Agents

Agents that suppress gene expression can be used to suppress the expression of genes encoding integrin subunits $\beta 1$, $\alpha 2$, $\alpha 6$ or $\alpha v$. Antisense agents can also be used to suppress expression of certain ligands thereto, such as laminin. Suppression of laminin expression can achieve similar effects to treatment with antibodies against laminin. Administration of the antisense reagents of the invention to a target cell or patient results in reduced activity of one of the above integrin genes or its ligand. For general methods relating to antisense polynucleotides, see, e.g., Antisense RNA and DNA, (1988), D. A. Melton, Ed., Cold Spring Harbor Laboratory, Cold Spring Harbor, N.Y.); Dagle et al., Nucleic Acids Research, 19:1805 (1991); Uhlmann et al., *Chem. Reviews*, 90:543-584 (1990). Ribozymes are another antisense agent that can suppress gene expression.

Antisense oligonucleotides can cause suppression by binding to, and interfering with the translation of sense mRNA, rendering mRNA susceptible to nuclease digestion, interfering with transcription, interfering with the processing or localization of RNA precursors, repressing the transcription of mRNA, or acting through some other mechanism. The particular mechanism by which the antisense molecule reduces expression is not critical.

Typically antisense polynucleotides comprise an antisense sequence of at least 7 to 10 to typically 20 or more nucleotides that specifically hybridize to a sequence from an mRNA of a gene. Some antisense polynucleotides are from about 10 to about 50 nucleotides in length or from about 14 to about 35 nucleotides in length. Some antisense polynucleotides are polynucleotides of less than about 100 nucleotides or less than about 200 nucleotides. In general, the antisense polynucleotide should be long enough to form a stable duplex, but short enough, depending on the mode of delivery, to administer in vivo, if desired. The minimum length of a polynucleotide required for specific hybridization to a target sequence depends on several factors, such as the G/C content, the positioning of mismatched bases (if any), the overall differences of the sequence relative to the population of target polynucleotides, and the chemical nature of the polynucleotide (e.g., methylphosphonate backbone, peptide nucleic acid, phosphorothioate), among other factors.

Suitable conditions for hybridizing complementary nucleic acid molecules are well known to those of skill in the art. For example, hybridization under typical high stringency conditions may be performed in a mixture containing 5×SSPE, 5× Denhart solution, 0.5% SDS (w/v), and 100 µg/ml salmon sperm DNA. The DNA is allowed to hybridize for a specified period of time at about 68° C. The hybridized DNA, which is typically bound to a membrane or filter, is then washed 2 times for 10 minutes, in 2×SSPE, 0.1% SDS (w/v) at room temperature. The membrane (or filter) is then immersed in a solution of 1×SSPE, 0.1% SDS (w/v) for 15 minutes at 68° C., and finally in a solution of 1×SSPE, 0.1% SDS (w/v) for 15 minutes at 68° C.

To ensure specific hybridization, the antisense sequence is at least substantially complementary to the target mRNA or gene encoding the same. Some antisense sequences are exactly complementary to their intended target sequence. The antisense polynucleotides can also include, however, nucleotide substitutions, additions, deletions, transitions, transpositions, or modifications, or other nucleic acid sequences or non-nucleic acid moieties so long as specific binding to the relevant target sequence corresponding to the RNA or its gene is retained as a functional property of the polynucleotide.

Some antisense sequences are complementary to relatively accessible sequences of mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Another useful method for identifying effective antisense compositions uses combinatorial arrays of oligonucleotides (see, e.g., Milner et al., *Nature Biotechnology*, 15:537 (1997).

One technique to inhibit gene expression involves the introduction of double-stranded RNA, also referred to as inhibitory RNA (RNAi), into a cell. The RNAi comprises two complementary strands of RNA (a sense strand and an antisense strand) annealed to each other to form a double stranded RNA molecule. The RNAi is typically derived from an exon or coding sequence of the gene that is being targeted for inhibition. The RNAi results in the destruction of mRNA complementary to the sequence of the RNAi molecule. Examples of RNAi and their use in living organisms are described, for example, by Fire et al., *Nature*, 391:806-811 (1998); Nykänen et al., *Cell*, 107:309-321 (2001); and in WO 01/29058, WO 01/75164, and WO 99/32619. In some methods the RNAi is between about 100 bp and 1000 bp, for example, about 100, 200, 300, 400, 500, 600, 700, 800, 900, 1000, or more base pairs. In some methods the RNAi is derived from an exon. In other methods, the RNAi is derived from an intron or signaling sequence.

In some methods, antisense polynucleotides have sequences in addition to the antisense sequence, including promoters and other regulatory sequences that result in expression of an antisense sequence. Provided that the promoter and, preferably termination and polyadenylation signals, are properly positioned, the strand of the inserted sequence corresponding to the noncoding strand is transcribed and acts as an antisense oligonucleotide. In some methods, the polynucleotide consists essentially of, or is, the antisense sequence. The antisense nucleic acids (DNA, RNA, modified, analogues, and the like) can be made using any suitable method for producing a nucleic acid, such as the chemical synthesis and recombinant methods disclosed herein. For example, antisense RNA molecules can be prepared by de novo chemical synthesis or by cloning.

Zinc finger proteins can be used as an alternative or in addition to antisense polynucleotides to suppress the expression of the genes encoding the β1, α2, α6 or αv integrin subunits. Zinc finger proteins can also be used to suppress the expression of certain ligands of these integrin subunits, such as laminin. Zinc finger proteins can also be used to activate or enhance the expression of other ligands, such as fibronectin, that can themselves be used as agents in the present methods. Zinc finger proteins can be engineered or selected to bind to any desired target site within a target gene. In some methods, the target site is within a promoter or enhancer. In other methods, the target site is within the structural gene. In some methods, the zinc finger protein is linked to a transcriptional repressor, such as the KRAB repression domain from the human KOX-1 protein (Thiesen et al., *New Biologist*, 2, 363-374 (1990); Margolin et al., *Proc. Natl. Acad. Sci. U.S.A.*, 91, 4509-4513 (1994)); Pengue et al., *Nucl. Acids Res.*, 22:2908-2914 (1994); Witzgall et al., *Proc. Natl. Acad. Sci. U.S.A.*, 91, 4514-4518 (1994). Preferred domains for achieving activation include the HSV VP 16 activation domain (see, e.g., Hagmann et al., *J. Virol.*, 71:5952-5962 (1997)) nuclear hormone receptors (see, e.g., Torchia et al., *Curr. Opin. Cell. Biol.*, 10:373-383 (1998)); the p65 subunit of nuclear factor kappa B (Bitko & Barik, *J. Virol.*, 72:5610-5618 (1998) and Doyle & Hunt, *Neuroreport*, 8:2937-2942 (1997)); Liu et al., *Cancer Gene Ther.*, 5:3-28 (1998)), or artificial chimeric functional domains such as VP64 (Seifpal et al., *EMBO J.*, 11:4961-4968 (1992)). Methods for selecting target sites suitable for targeting by zinc finger proteins, and methods for designing zinc finger proteins to bind to selected target sites are described in WO 00/00388. Methods for selecting zinc finger proteins to bind to a target using phage display are described by EP 95908614A. Methods for using zinc finger proteins to regulate endogenous genes are described in WO 00/00409. Zinc finger proteins can be administered either as proteins or in the form of nucleic acids encoding zinc fingers and having appropriate regulatory sequences.

D. Nucleic Acids Encoding Therapeutic Agents

Antibody or other peptide reagents can be administered in the form of nucleic acids encoding antibody chains or peptides. Such nucleic acids are typically linked to regulatory elements, such as a promoter and enhancer, that allow expression of the DNA segment in the intended target cells of a patient. Promoter and enhancer elements from light or heavy chain immunoglobulin genes or the cytomegalovirus (CMV) major intermediate early promoter and enhancer are suitable to direct expression. In some methods promoters that cause expression in the brain are used. Promoters such as platelet-derived growth factor (PDGF), prion, or the neural enolase promoter are suitable.

The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, *Curr. Opin. Genet. Develop.*, 2:102-109 (1993)); adenoviral vectors (see, e.g., Bett et al., *J. Virol.*, 67:5911 (1993)); adeno-associated virus vectors (see, e.g., Zhou et al., *J. Exp. Med.*, 179:1867-75 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.*, 70:508-19 (1996)), Venezuelan equine encephalitis virus (see U.S. Pat. No. 5,643,576), rhabdoviruses, such as vesicular stomatitis virus (see WO 96/34625), and papillomaviruses (Ohe et al, *Human Gene Therapy*, 6:325-33 (1995); Woo et al., WO 94/12629; and Xiao & Brandsma, *Nucleic Acids. Res.*, 24:2630-22 (1996)).

DNA can be packaged into liposomes. Suitable lipids and related analogs are described by U.S. Pat. Nos. 5,208,036, 5,264,618, 5,279,833, and 5,283,185. Vectors and DNA encoding an immunogen can also be adsorbed to or associated with particulate carriers, examples of which include polymethyl methacrylate polymers, polylactides, and poly (lactide-co-glycolides).

Gene therapy vectors or naked DNA can be delivered in vivo by administration to an individual patient, typically by systemic administration (e.g., intravenous, intraperitoneal, nasal, gastric, intradermal, intramuscular, intrathecal, subdermal, or intracranial infusion) or topical application (see, e.g., U.S. Pat. No. 5,399,346). Such vectors can further include facilitating agents such as bupivacine (U.S. Pat. No. 5,593, 970). DNA can also be administered using a gene gun. See Xiao & Brandsma, supra. The DNA is precipitated onto the surface of microscopic metal beads. The microprojectiles are accelerated with a shock wave or expanding helium gas, and penetrate tissues to a depth of several cell layers. For example, the Accel™ Gene Delivery Device manufactured by Agacetus, Inc., Middleton, Wis. is suitable. Alternatively, naked DNA can pass through skin into the blood stream simply by spotting the DNA onto skin with chemical or mechanical irritation (see WO 95/05853).

In a further variation, nucleic acids can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells that have incorporated the vector.

IV. Patients Amenable to Treatment

The present methods are useful for prophylactic or therapeutic treatment of several amyloidogenic diseases and conditions that are characterized by the presence of deposits of amyloid proteins, such as amylin or A$\beta$ peptide. Such diseases include Alzheimer's disease, Down's syndrome and cognitive impairment, type II diabetes, Parkinson's disease, amyloidoses such as hereditary or systemic amyloidoses, and diseases caused all or in part by prion infection. Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, for example mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia, or arteriosclerosis. Individuals presently suffering from Alzheimer's disease can be recognized from characteristic dementia, as well as the presence of the risk factors described above. In addition, a number of diagnostic tests are available for identifying individuals who have AD. These include measurement of cerebrospinal fluid (CSF) tau and A$\beta$42 levels. Elevated tau and decreased A$\beta$42 levels signify the presence of AD. Individuals suffering from Alzheimer's disease can also be diagnosed by ADRDA criteria. In asymptomatic patients, treatment can begin at any age (e.g., about 10, about 20, about 30). Usually, however, it is not necessary to begin treatment until a patient reaches about 40, about 50, about 60, about 70, about 80 or about 90. Treatment typically entails multiple dosages over a period of time. In the case of Down's syndrome patients, treatment can begin prenatally by administering therapeutic agents to the mother; or treatment may begin shortly after birth.

V. Treatment Regimes

In prophylactic applications, pharmaceutical compositions or medicaments are administered to a patient susceptible to, or otherwise at risk of developing an amyloidogenic disease, in an amount sufficient to eliminate or reduce the risk, lessen the severity, or delay the onset of the disease, including biochemical, histological and/or behavioral symptoms of the disease, its complications and intermediate pathological phenotypes presenting during development of the disease.

In therapeutic applications, compositions or medicaments are administered to a patient suspected of, or already suffering from such a disease in an amount sufficient to cure, or at least partially arrest, the symptoms of the disease (biochemical, histological, and/or behavioral), including its complications and intermediate pathological symptoms. An amount adequate to accomplish therapeutic or prophylactic treatment is defined as a therapeutically- or prophylactically-effective dose. In therapeutic regimes, the agent is usually administered at intervals until symptoms of the disease disappear or significantly decrease. Optionally administration can be continued to prevent recurrence. In prophylactic regimes, agents are also usually administered at intervals, in some instances for the rest of a patient's life. Treatment can be monitored by assaying levels of administered agent, or by monitoring the response of the patient. The response can be monitored by ADRDA criteria and imaging of plaques in the brain of the patient (see WO 00/14810).

Effective doses of the compositions of the present invention, for the treatment of the above-described conditions vary depending upon many different factors, including means of administration, target site, physiological state of the patient, whether the patient is human or an animal, other medications administered, and whether treatment is prophylactic or therapeutic. Usually, the patient is a human; nonhuman mammals, including transgenic mammals, can also be treated. Treatment dosages are typically titrated to optimize safety and efficacy.

Dosages of antibodies, peptides, and small molecules range from about 0.0001 to about 100 mg/kg, and more usually about 0.01 to about 20 mg/kg, of the host body weight. For example, dosages can be about 1 mg/kg body weight or about 20 mg/kg body weight or within the range of about 1 to about 10 mg/kg. An exemplary treatment regime entails administration once per every two weeks or once a month or once every 3 to 6 months. In some methods, two, three, four or more monoclonal antibodies with different binding specificities are administered simultaneously, in which case the dosage of each antibody administered falls within the ranges indicated. For example, in some methods antibodies to two or all three of β1 integrin, α2 integrin, and αv integrin subunits are administered simultaneously. In some methods, antibodies to the α6 integrin subunit are also administered. Antibody is usually administered on multiple occasions. Intervals between single dosages can be weekly, monthly or yearly. Intervals can also be irregular as indicated by measuring blood levels of antibody to integrins in the patient. In some methods, dosage of antibody is adjusted to achieve a plasma antibody concentration of about 1 to about 1000 μg/ml, and in some methods about 25 to about 300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until the progression of the disease is reduced or terminated, and preferably until the patient shows partial or complete amelioration of the symptoms of the disease. Thereafter, the patient can be administered a prophylactic regime.

Doses for nucleic acid encoding agents range from about 10 ng to 1 g, about 100 ng to about 100 mg, about 1 μg to about 10 mg, or about 30 to about 300 μg DNA per patient. Doses for infectious viral vectors may vary from about 10 to about 100, or about $10^3$, about $10^4$, about $10^5$, about $10^6$, about $10^7$, about $10^8$, about $10^9$, about $10^{10}$, or more virions per dose.

Agents of the invention can be administered by parenteral, topical, intravenous, oral, subcutaneous, intrathecal, intraarterial, intracranial, intraperitoneal, intranasal, or intramuscular means for prophylactic and/or therapeutic treatment. In some methods, agents are injected directly into a particular tissue where deposits have accumulated, for example, intracranial injection. In some methods, intramuscular injection or intravenous infusion are employed for the administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in the treatment of amyloidogenic disease. In the case of Alzheimer's disease and Down's syndrome, in which amyloid deposits occur in the brain, agents of the invention can also be administered in conjunction with other agents that increase passage of the agents of the invention across the blood-brain barrier.

Agents of the invention are often administered as compositions comprising an active therapeutic agent and a variety of other pharmaceutically acceptable components. See *Remington's Pharmaceutical Science* (15th ed., Mack Publishing Company, Easton, Pa., 1980). The particular formulation employed depends on the intended mode of administration and the therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to negatively impact the biological activity of the combination. Examples of such diluents include, but are not limited to, distilled water, physiological phosphate-buffered saline, Ringer's solution, dextrose solution, and Hank's solution. In addition, the pharmaceutical composition or formulation may also include other carriers, adjuvants, or nontoxic, nontherapeutic, nonimmunogenic stabilizers, and the like.

Pharmaceutical compositions can also include large, slowly metabolized macromolecules such as proteins, polysaccharides such as chitosan, polylactic acids, polyglycolic acids, copolymers (such as latex functionalized Sepharose™ beads, agarose, cellulose, and the like), polymeric amino acids, amino acid copolymers, and lipid aggregates (such as oil droplets or liposomes).

For parenteral administration, agents of the invention can be administered as injectable dosages of a solution or suspension of the substance in a physiologically-acceptable diluent with a pharmaceutical carrier that can be a sterile liquid such as water, oils, saline, glycerol, or ethanol. Parenteral compositions for human administration are sterile, substantially isotonic, and made under GMP conditions. Additionally, auxiliary substances, such as wetting or emulsifying agents, surfactants, pH buffering substances, and the like, can be present in compositions. Other components of pharmaceutical compositions are those of petroleum, animal, vegetable, or synthetic origin, for example, peanut oil, soybean oil, and mineral oil. In general, glycols, such as propylene glycol or polyethylene glycol, are preferred liquid carriers, particularly for injectable solutions. Antibodies can be administered in the form of a depot injection or implant preparation that can be formulated in such a manner as to permit a sustained release of the active ingredient. An exemplary composition comprises monoclonal antibody at 5 mg/mL, formulated in aqueous buffer containing 50 mM L-histidine (optional), 150 mM NaCl, adjusted to a suitable pH with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect, as discussed above (see Langer, *Science*, 249:1527-33 (1990) and Hanes et al., *Advanced Drug Delivery Reviews*, 28:97-119 (1997). The agents of this invention can be administered in the form of a depot injection or implant preparation that can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of about 0.5% to about 10%, or about 1% to about 2%. Oral formulations include, but are not limited to, excipients such as pharmaceutical grades of mannitol, lactose, starch, magnesium stearate, sodium saccharine, cellulose, and magnesium carbonate. These compositions typically take the form of solutions, suspensions, tablets, pills, capsules, sustained release formulations or powders and contain about 10% to about 95% of active ingredient, or about 25% to about 70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature, 391:851 (1998)). Coadministration can be achieved by using the components as a mixture or as linked molecules obtained by chemical crosslinking or expression as a fusion protein. Alternatively, transdermal delivery can be achieved using a skin patch or using transferosomes (Paul et al., Eur. J. Immunol., 25:3521-24 (1995); Cevc et al., Biochem. Biophys. Acta, 1368:201-15 (1998)).

EXAMPLES

Materials and Methods for Examples 1-5

Sources of Antibody

| Antibody | Source | Antigen | Ligand blocked |
|---|---|---|---|
| MAB1998 | Chemicon | human α2 integrin | collagen and laminin |
| MAB1950Z | Chemicon | human α2 integrin | collagen and laminin |
| Gi9 | Immunotech | human α2 integrin | collagen |
| VNR147 | Gibco or Chemicon | human αV integrin | fibrinogen and vitronectin |
| MAB1980 | Chemicon | human αV integrin | vitronectin |
| IM1603 | Immunotech | human αV integrin | vitronectin |
| Lia1/2 | Immunotech | human β1 integrin | fibronectin |
| MAB1965 | Chemicon | human β1 integrin | collagen and fibronectin |
| AIIB2 | Caroline Damsky, UCSF | Human β1 integrin | fibronectin |
| AB19012 | Chemicon | human laminin | laminin |
| AB2034 | Chemicon | mouse laminin | laminin |

Tissue Culture

Tissue culture plates were coated with polyethyleneimine (PEI) in 150 mM sodium borate, pH 8.5, and incubated overnight at room temperature. Prior to adding cells, the wells were washed with PBS and Minimal Essential Media (MEM with 10% FBS) was added until cells were ready for plating. Human fetal cerebral cortex (E13-E16) was rinsed with Hank's Balanced Salt Solution (HBSS). Tissue was triturated in 1 mg of DNAse in HBSS. This suspension was filtered through a 100 micron nylon cell strainer and spun at 250×g for 5 minutes. The cells were resuspended in trypsin and incubated at 37° C. for 20 minutes. Modified Minimal Essential Media (MMEM with 10% FBS and 1 mg of DNase) was added and the cells were resuspended; then collected again by centrifugation. Cells were resuspended in MMEM containing B27, and plated in washed PEI-coated plates at 125,000 cells/well in 96 well plates or at 2.5 million cells/well in 6 well plates. The human cortical cultures (HCC) were incubated for 3 weeks with biweekly medium exchanges prior to treatment.

Aβ Generation

Aβ was generated by adding double distilled water (ddH$_2$O) to Aβ to make up a 1 mM stock. This was aged for 3 days at 37° C., aliquoted, and stored frozen at −20° C. Soluble Aβ was made by adding DMSO to Aβ to make a 7.5 mM stock, sonicating for 30 minutes, aliquoting, and freezing at −20° C. Neurotoxic Aβ was generated by adding ddH$_2$O to Aβ, aliquoting, and freezing at −20° C.

Integrin Immunoprecipitations from HCC Lysates

HCC in 6 well plates were labeled with 100 μCi/ml $^{35}$S-Methionine in methionine-free medium overnight. Cells were washed, lysed with 25 mM Hepes, pH 7.5, 1% Triton X-100, 0.1% SDS, 150 mM NaCl, 0.5 mM EDTA, 0.5 mM EGTA, and passed through a 26 gauge needle three times. Insoluble material was removed by centrifugation at 15,000 rpm for 15 minutes at 4° C. Lysates were pre-cleared on rabbit anti-mouse (RAM) antibody coupled to protein A beads and immunoprecipitated with integrin subunit-specific antibodies (Lia1/2 for β1, TS2/7 for α1, Gi9 for α2, P1B5 for α3, AN100226m for α4, Ab0771 for α5, GoH3 for α6, Y9A2 for α9, and VNR147 for αv). Immunoprecipitates were washed 3 times with 1 ml of 25 mM Hepes, pH 7.5, 1% Triton X-100 150 mM NaCl, 0.5 mM EDTA, and 0.5 mM EGTA. Immunoprecipitated samples were separated on 8% tris-glycine gels (Novex) and fixed; gels were dried, and the $^{35}$S-labeled proteins in the gels were visualized by autoradiography.

Aβ Immunofluorescence

HCC treated with Aβ for 72 hours were fixed with 4% paraformaldehyde, stained with 5 μg/ml anti-Aβ-3D6-biotin, and visualized with 10 μg/ml streptavidin-FITC (Jackson).

Aβ Neurotoxicity in Human Cortical Neurons

HCC were pretreated with antibodies or ligands for 30 minutes in neuronal medium (MEM) supplemented with glutamine and penicillin/streptomycin (basal media). One micromolar Aβ in basal medium was added for 1 hour. The medium was removed and the HCC were treated with antibodies or ligands and 20 μM soluble Aβ in basal medium for 3 days. At three days, the toxicity was determined by incubating in 10% alamar blue in basal medium for two hours. Fluorescence levels were measured relative to control and Aβ treated wells in triplicate.

Integrin Heterodimer Associations

HCC in 6-well plates in MMEM media supplemented with N-2 (Bottenstein's N-2 Formulation, e.g., Catalog #17502, Invitrogen Corp., Carlsbad, Calif.) were placed on wet-ice, washed with PBS, lysed with 25 mM Hepes, pH 7.5, 1% Triton X-100, 0.1% SDS, 150 mM NaCl, 0.5 mM EDTA, and 0.5 mM EGTA, and passed through a 26 gauge needle 3 times. Insoluble material was removed by centrifugation at 15,000 rpm for 15 minutes at 4° C. Lysates were precleared on protein A beads and β1 integrin immunoprecipitated using anti-β1 integrin, Lia1/2 (Immunotech), and RAM/protein G beads (Pharmacia). Immunoprecipitates were washed 3 times with 1 ml of 25 mM Hepes, pH 7.5, 1% Triton X-100 150 mM NaCl, 0.5 mM EDTA, and 0.5 mM EGTA. Immunoprecipitated samples were separated on 4-12% tris-glycine gels (Novex) and Western-blotted with anti-α2 integrin (AB 1936 from Chemicon) or with anti-αv integrin, MAB 1960 (Chemicon).

Aβ Induction of Paxillin Phosphorylation

Neurotoxic Aβ was added to HCC in 6-well plates in basal media supplemented with N-2 for 0 minutes to 24 hours. HCC was placed on wet-ice, washed with PBS, lysed with 25 mM Hepes, pH 7.5, 1% Triton X-100, 0.1% SDS, 150 mM NaCl, 0.5 mM EDTA, and 0.5 mM EGTA, and passed through a 26 gauge needle 3 times. Insoluble material was removed by centrifugation at 15,000 rpm for 15 minutes at 4° C. Lysates were precleared on protein A beads and Fak or Pyk2 immunoprecipitated using anti-Fak (UBI) or anti-Pyk2 antibody (UBI), respectively, and protein A beads. Immunoprecipitates were washed 3 times with 1 ml of 25 mM Hepes, pH 7.5, 1% Triton X-100 150 mM NaCl, 0.5 mM EDTA, and 0.5 mM EGTA. Immunoprecipitated samples were separated on 8% tris-glycine gels (Novex) and Western blotted with anti-phosphotyrosine (RC20 from Transduction labs) and with anti-paxillin (Transduction labs).

Example 1

Immunofluorescence Pattern on Human Cortical Neurons

The present examples produce an in vitro tissue culture model of Aβ plaques that form on hippocampal and cortical neurons in Alzheimer's disease (AD) and exhibit the associated neurotoxicity. The model uses primary human cortical neuronal cultures to represent the neurons effected in AD as closely as possible. Addition of Aβ to these cultures results in a reproducible Aβ meshwork that forms over 1-3 days on the neurons and subsequently causes toxicity in the neurons. Aβ incubated on plates without HCC also stained as a meshwork but consistently showed a more uniform pattern with extensions that were shorter, thinner, and more linear than those seen on HCC. FIGS. 1A and 1B compare the meshwork in the presence and absence of HCC.

Example 2

β1 Integrin Mediates Aβ Meshwork and Neurotoxicity

Figure 2C:
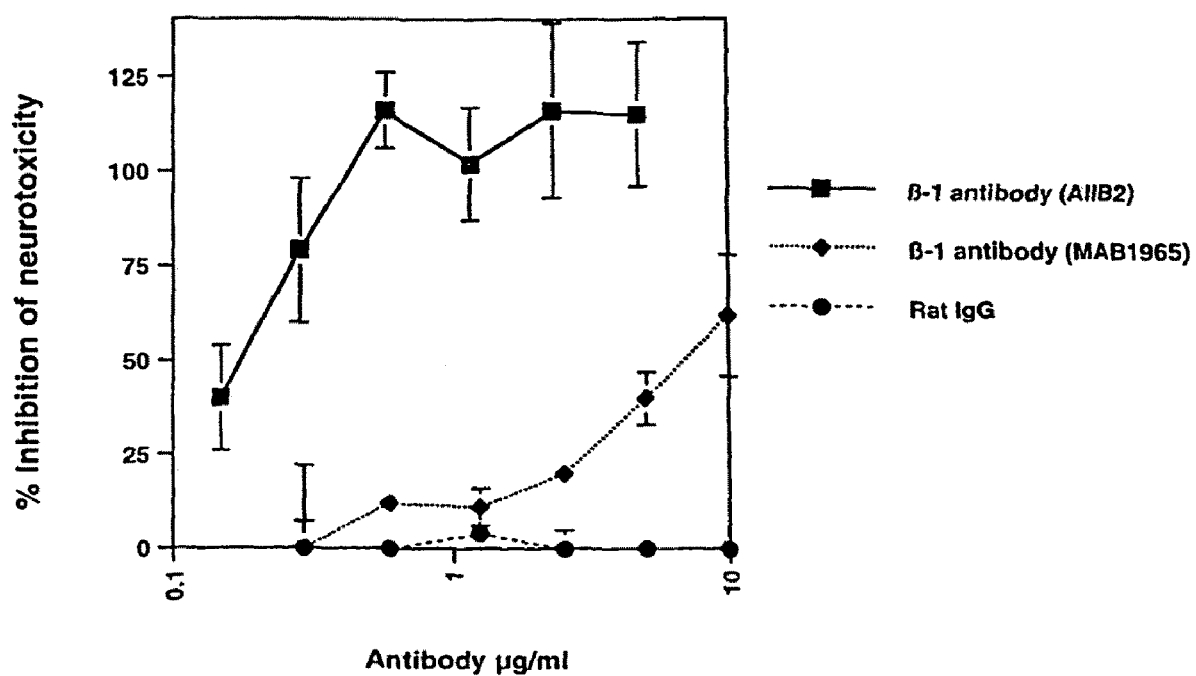
FIG. 2C illustrates the inhibition of neurotoxicity in HCC preincubated with β1 integrin subunit blocking antibodies. Error bars represent standard deviation from (n=3) wells.

Because the meshwork resembled an extracellular matrix, like those formed by integrin, it was investigated whether integrin was present in the HCC; and if so, if integrin facilitated the Aβ meshwork formation on HCC. Gel electrophoresis showed that β1 integrin is expressed in HCC. It was also found that β1 integrin blocking antibodies, including MAB1965, could block the Aβ meshwork pattern from forming on HCC (compare FIG. 2A (without antibody) to FIG. 2B (with antibody)). Whether the meshwork pattern was necessary for the toxicity generated by Aβ in these cultures was also investigated. To test this, HCC were incubated with β1 integrin blocking antibodies (AIIB2 and MAB1965) that had been shown to block the Aβ meshwork. These antibodies also blocked Aβ induced toxicity in a dose dependent manner (FIG. 2C). The antibody AIIB2 is a very potent blocker of Aβ toxicity, exhibiting an $IC_{50}$ of 170 ng/ml or 1 nM. In contrast, a control antibody had no effect on toxicity.

Example 3

Figure 3A:
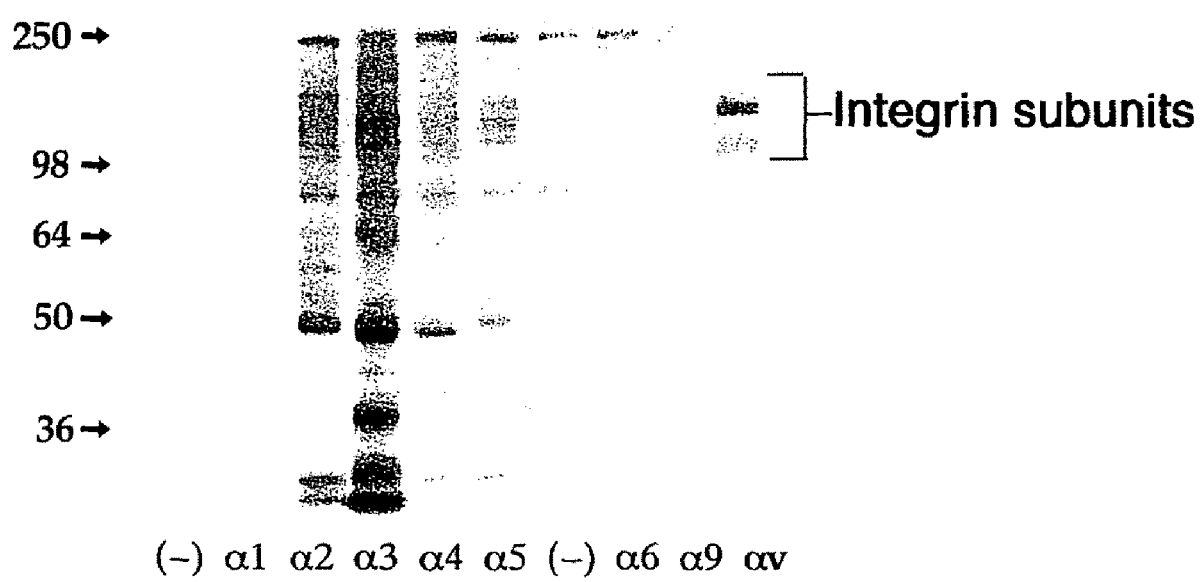
FIG. 3A illustrates the effects of α2 and αv integrin subunits on Aβ meshwork formation and neurotoxicity in HCC.
Figure 3B:
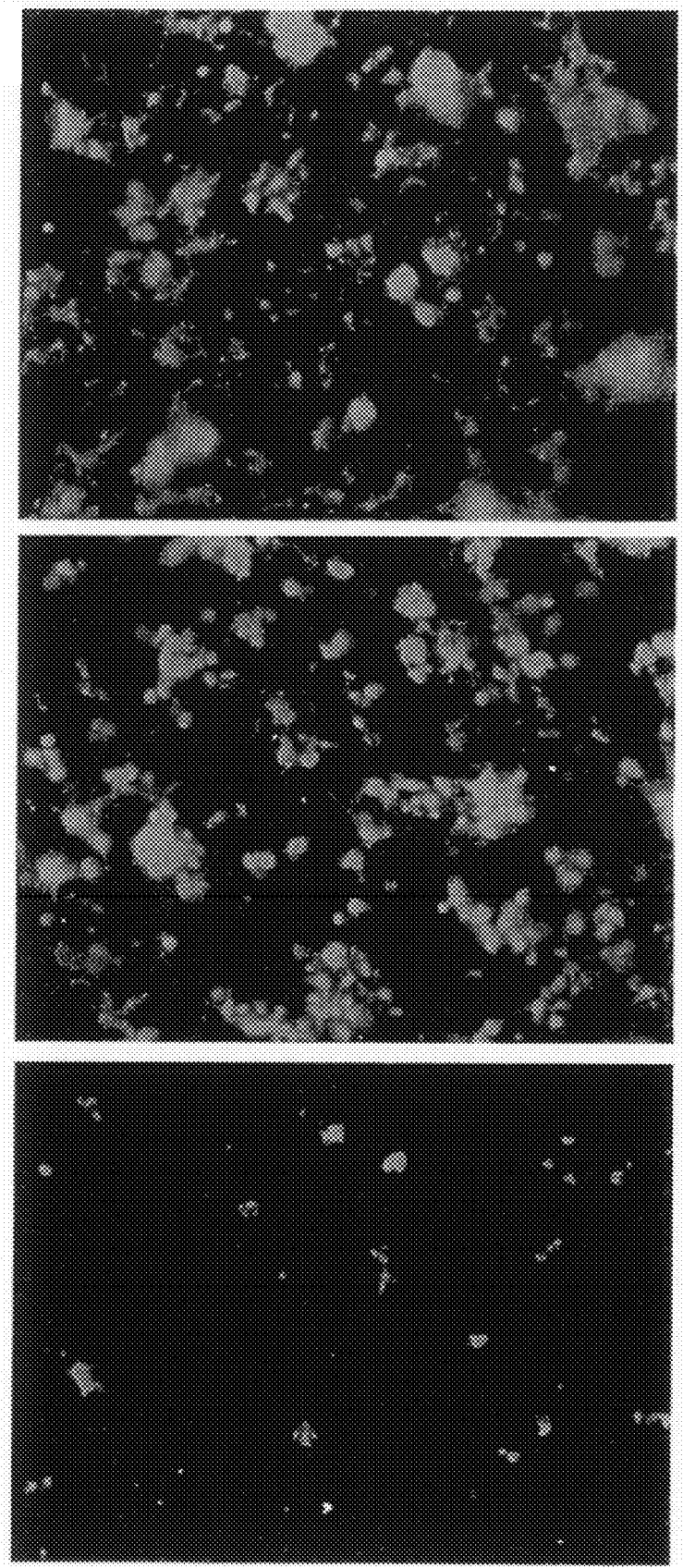
FIG. 3B illustrates 72 hour Aβ meshwork formation in HCC preincubated in the absence (top) or presence of anti-α2 (middle) or anti-αv (bottom) antibodies.
Figure 4:
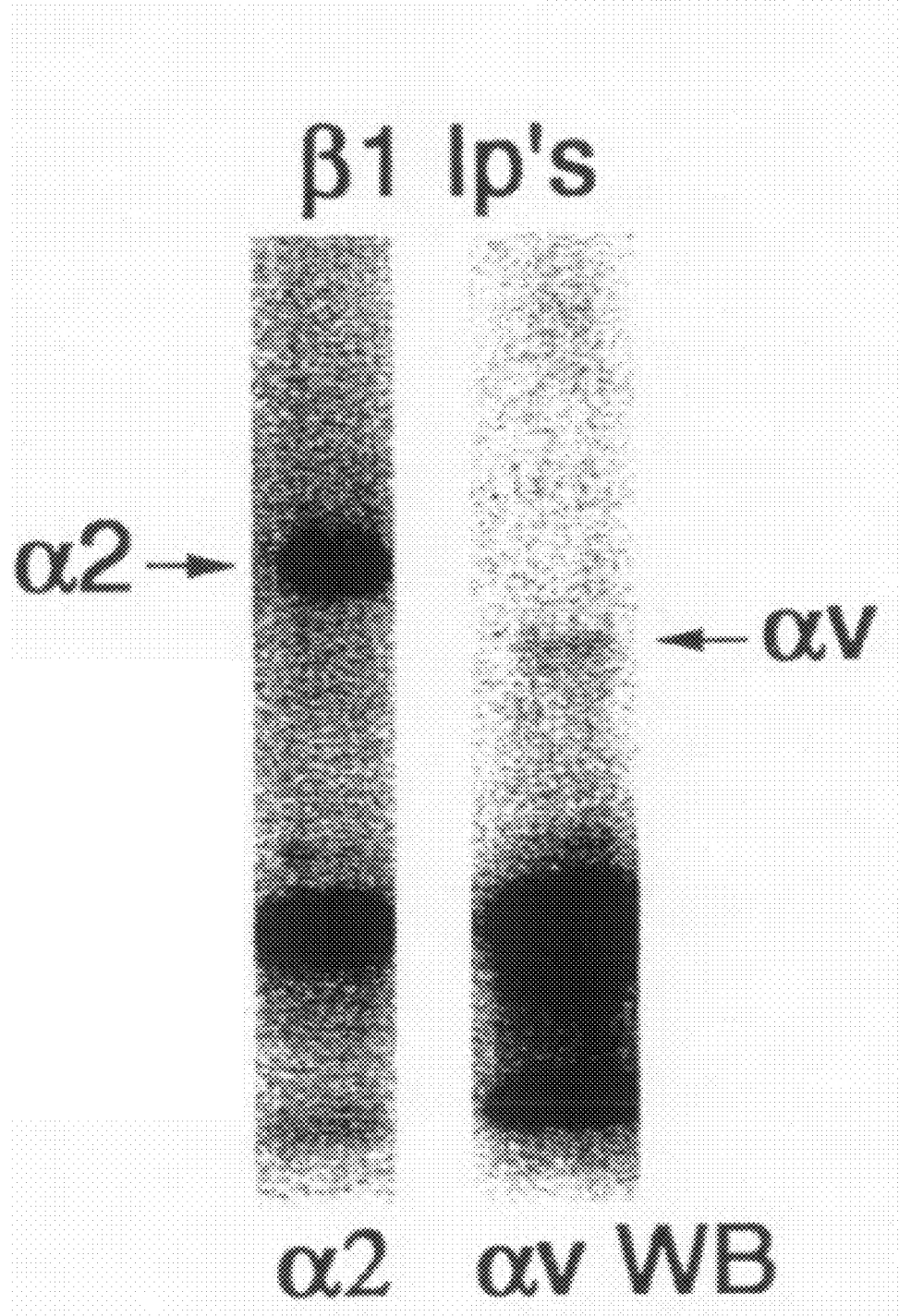
FIG. 4 illustrates α2 and αv expression in HCC.

Agents that Bind to α2 and αv Integrins Inhibit Meshwork and Aβ-Mediated Neurotoxicity β1 integrin can pair with several α subunits to form different heterodimers. It was therefore tested which a integrin subunits were present in the HCC. The α2, α3, α4, α5, α6, and αv integrins were expressed in HCC. The α1 and α9 integrins were not expressed in HCC. Inhibitory antibodies against all these alpha integrin subunits were tested for their ability to inhibit Aβ meshwork formation and to inhibit its neurotoxicity. Inhibitory antibodies to α2 and αv inhibited Aβ meshwork formation (FIG. 3A). These antibodies also inhibited Aβ's neurotoxic effect in HCC (FIG. 3B). To show specificity to these particular integrins, 2-3 inhibitory antibodies were tested against each of these integrins and against the other integrin subunits as well. A very clear specificity to α1, α2, and αv integrins, mediating both the meshwork formation and neurotoxicity, was found (Table 1).

TABLE 1

Aβ meshwork and neurotoxicity inhibition with integrin blocking antibodies and ligands

| Antibody: | Meshwork Inhibition | Maximal inhibition of toxicity (%) |
|---|---|---|
| β1 integrin: | | |
| AIIB2 | ND | 100 |
| 1965 | Yes | 100 |
| Lia1/2 | Yes | 80 |
| TS2/16 (activating) | ND | 0 |
| α1 integrin: | | |
| TS2/7 | ND | 5 |
| 1973Z | ND | 6 |
| α2 integrin: | | |
| Gi9 | Yes | 100 |
| 1950Z | Yes | 100 |
| 1998 | ND | 25 |
| α3 integrin: | | |
| 1952Z | ND | 10 |
| 2056 | ND | 10 |
| 2057 | ND | 20 |
| α4 integrin: | | |
| AN100226m | ND | 10 |
| α5 integrin: | | |
| P1D6 | ND | 5 |
| SAM1 | No | 5 |
| α6 integrin: | | |
| GoH3 | ND | 40 |
| α9 integrin: | | |
| Y9A2 | No | 0 |
| αv integrin: | | |
| VNR147 | Yes | 100 |
| 1980 | Yes | 40 |
| IM1603 | ND | 20 |
| Fibronectin | Yes | 32 |
| Superfibronectin | Yes | 100 |
| Laminin | ND | 20 |
| NCAM antibody | No?? | 0 |

A weak but reproducible effect of an anti-α6 antibody on toxicity was observed. Finally, to confirm that these effects were directed against the integrins and not nonspecifically interfering with Aβ polymerization, Aβ toxicity was analyzed side-by-side in human and mouse cortical cultures. The antibodies used in these assays do not crossreact with mouse integrins. The anti-human integrin antibodies could inhibit Aβ toxicity in human cultures but not in mouse cultures, suggesting that the antibodies were not nonspecifically interacting with Aβ to inhibit toxicity. It was confirmed that α2 and αv were associated with β1 integrin in HCC cells by immunoprecipitating HCC lysates with a β1 antibody and then blotting the precipitated material with antibodies for α2 and αv. These results indicate that heterodimers of α2β1 and αvβ1 are functional mediators of Aβ meshwork formation and neurotoxicity.

Example 4

Figure 5B:
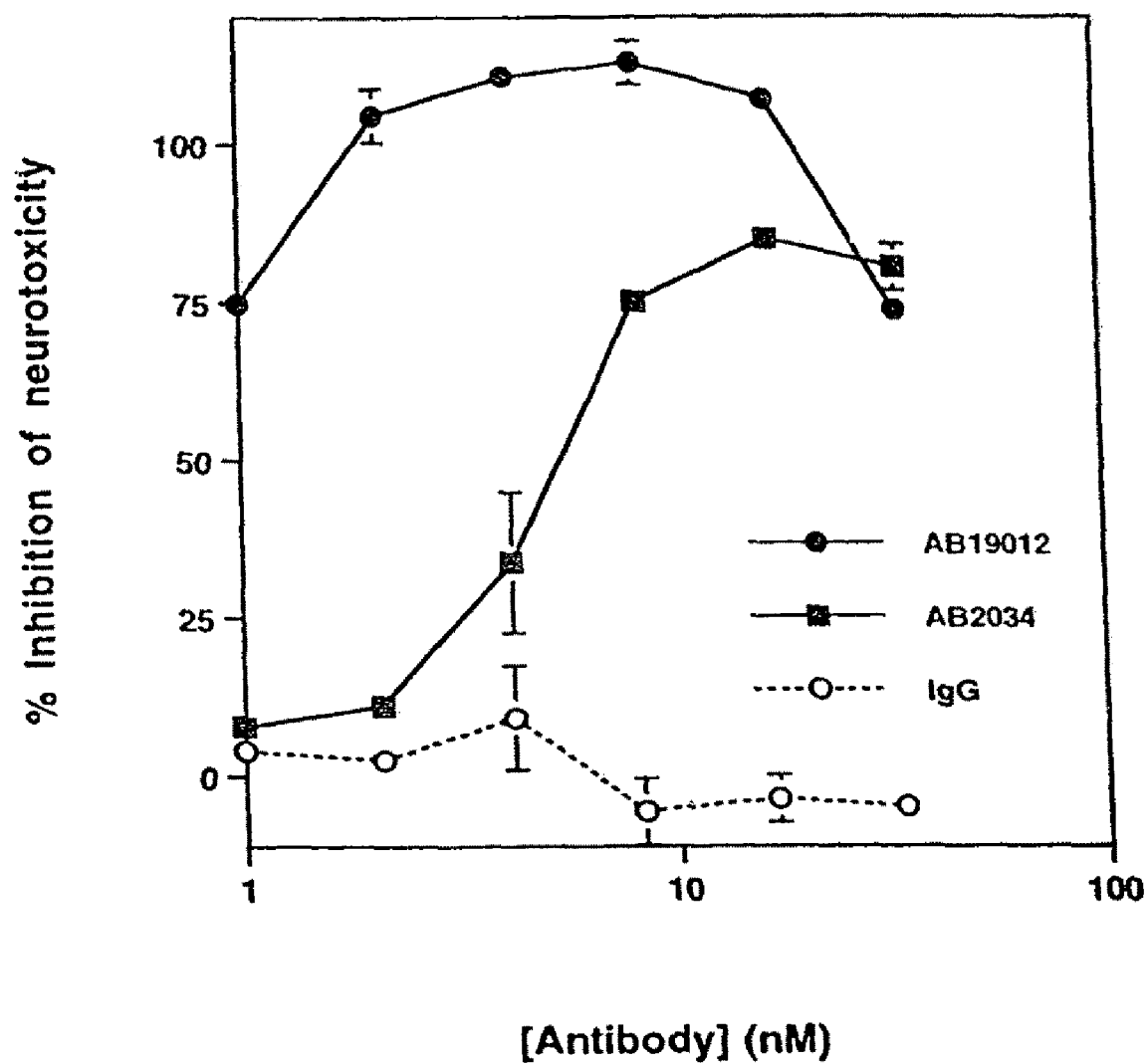
FIG. 5B illustrates neurotoxicity in HCC preincubated with anti-laminin antibodies. Error bars represent standard deviation from (n=3) wells.
Figure 5C:
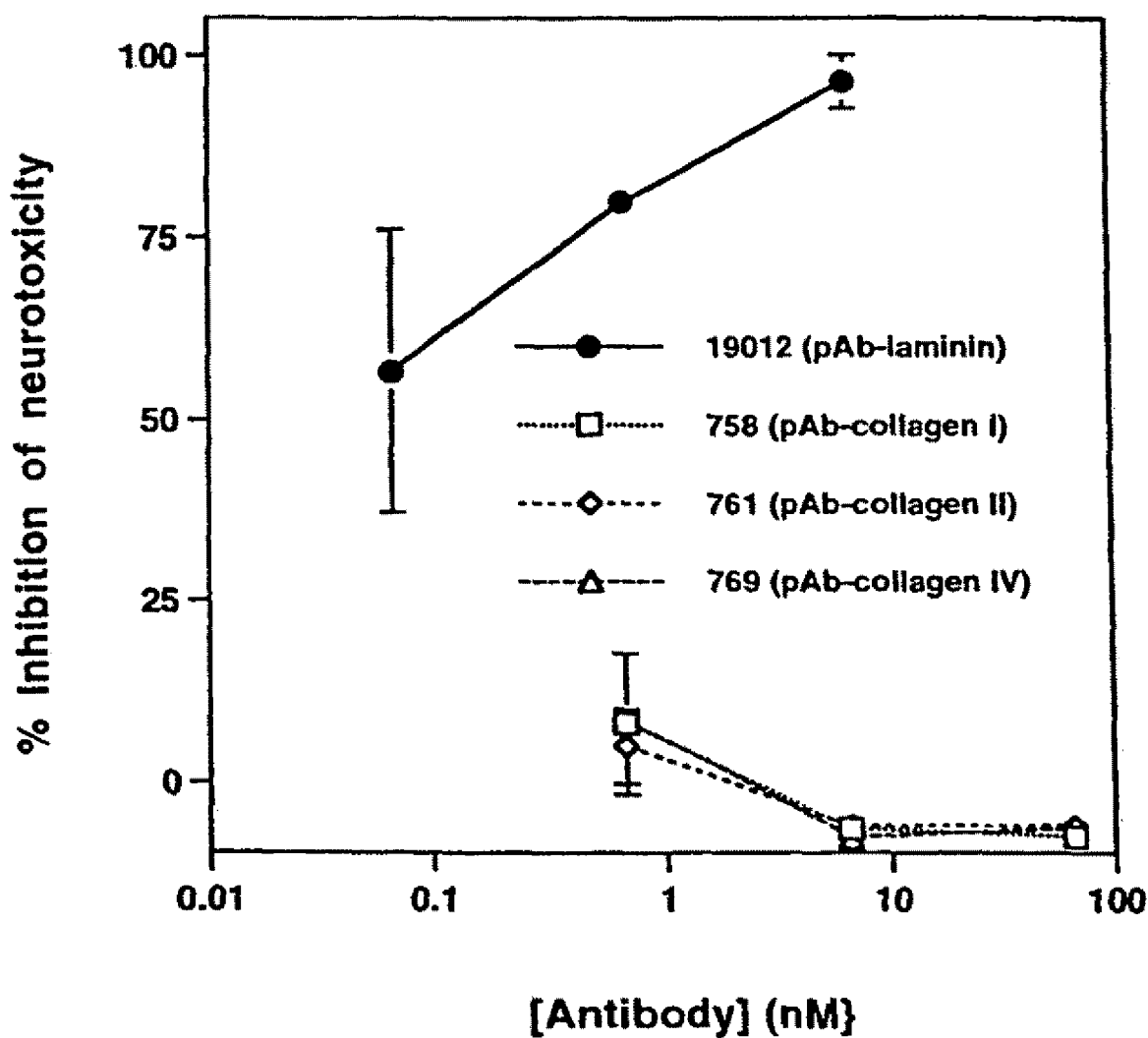
FIG. 5C illustrates neurotoxicity in HCC preincubated with anti-collagen antibodies. Error bars represent standard deviation from (n=3) wells.

Fibronectin and Anti-Laminin Antibodies Inhibit Aβ Meshwork Formation and Neurotoxicity Other components of the integrin/extracellular meshwork were investigated for involvement in mediating Aβ meshwork formation and neurotoxicity. These other components included the αvβ1 integrin ligands, fibronectin, and superfibronectin (multimers of fibronectin domain forming a meshwork), and the α2β1 ligands, collagen and laminin. Laminin has two chains β1 and γ1, both of which are elevated in Alzheimer's disease plaques (Murtomaki et al., *J. Neur. Res.*, 32:261-73 (1992)). Fibronectin and superfibronectin were capable of inhibiting Aβ meshwork formation and neurotoxicity (Table 1). This result can be explained by fibronectin competing with Aβ for effects on αvβ1 function. In contrast, an αvβ1 ligand, laminin, was not capable of inhibiting Aβ meshwork or neurotoxicity (Table 1). To determine why an αvβ1 ligand was protective, when an αvβ1 ligand was not, anti-laminin antibodies were tested in the meshwork formation and neurotoxicity assay. Two laminin antibodies were highly protective both in Aβ meshwork formation (FIG. 5A) and Aβ mediated neurotoxicity (FIG. 5B). The anti-laminin antibody #AB19012 showed an $IC_{50}$ of less than 1 nM. In contrast, anti-collagen antibodies, had no effect on Aβ meshwork formation and neurotoxicity (FIG. 5C).

Example 5

Figure 6A:
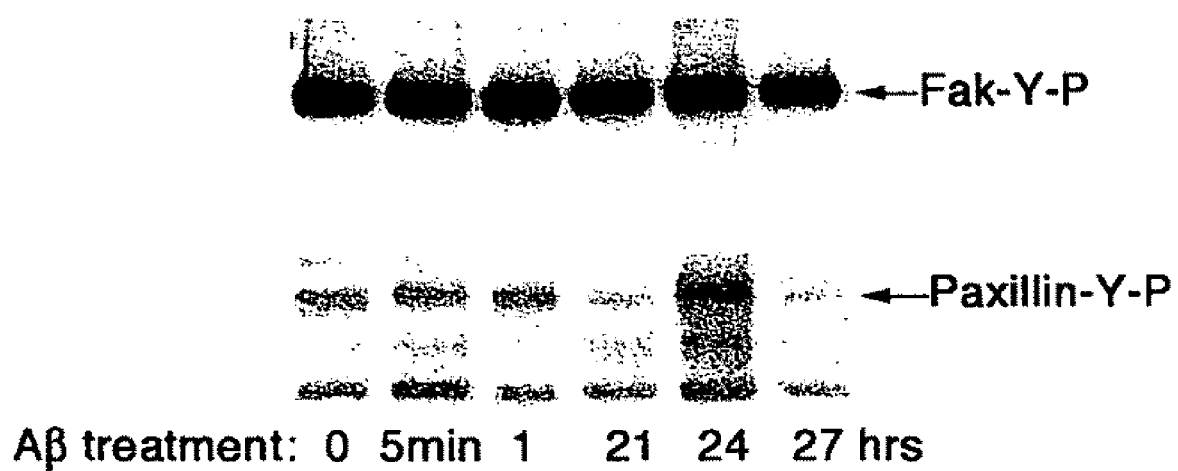
FIG. 6A illustrates tyrosine phosphorylation of focal adhesion kinase (Fak)-associated paxillin in Aβ treated HCC.
Figure 6B:
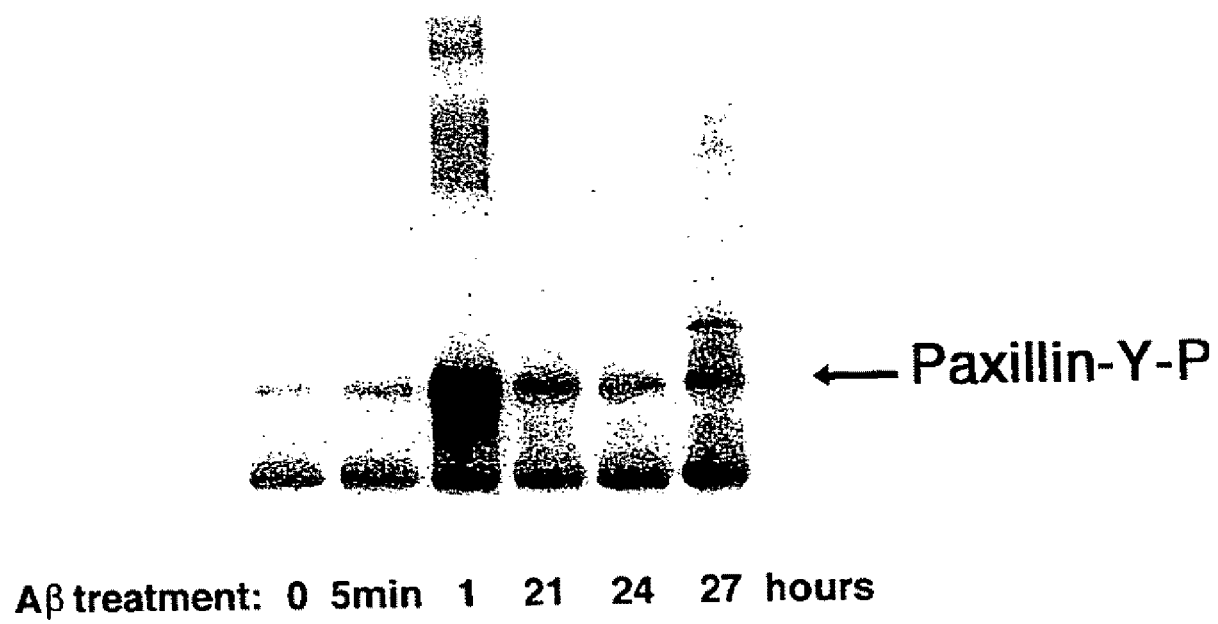
FIG. 6B illustrates tyrosine phosphorylation of proline-rich tyrosine kinase (Pyk2)-associated paxillin in Aβ treated HCC.

Aβ Activates Paxillin Tyrosine Phosphorylation, an Early Event in Integrin Signaling Pathways Integrin activation by an extracellular matrix ligand leads to the activation of focal adhesion kinases, such as Fak, and tyrosine phosphorylation of its substrate, paxillin. To determine if Aβ was similarly stimulating integrin signaling pathways, the tyrosine phosphorylation pattern of Fak-associated paxillin upon Aβ addition to HCC (FIG. 6A) was analyzed. Consistent activation of Fak-associated paxillin tyrosine phosphorylation was not found. However, a consistent increase in Pyk2-associated paxillin tyrosine phosphorylation subsequent to Aβ stimulation was observed. Pyk2 is also a focal adhesion kinase and may be mediating an aberrant Aβ/integrin signaling pathway that leads to neurotoxicity (FIG. 6B). The activation of Pyk2-, rather than Fak-associated paxillin tyrosine phosphorylation, may be what causes a toxic response in these conditions. In any case, Aβ activates paxillin tyrosine phosphorylation, an early event in integrin signaling pathways, indicating that the Aβ neurotoxic signal may be mediated through direct engagement of the α2β1 and αvβ1 integrin signaling pathways.

Example 6

Amylin Two Component Toxicity

Seed or aggregated amylin (1 mM) from CPR, Inc. (641-80, lot NG-0213) was made by adding 200 μl water/mg powder and then aging the solution for three days at 37° C. Soluble amylin (5 mM) was prepared by adding 40 μl DMSO/mg powder and sonicating the mixture for 30 minutes in a water bath. Both stock solutions were aliquoted and frozen until ready for use. Soluble amylin stock was diluted to 20 μM in culture medium just prior to use and filtered through an Amicon 30 filter that had been pre-washed with water. Filtered material was then diluted to its appropriate concentration.

Human cortical neurons (at 125,000 cells/96 well) were treated for 1 hour with seed amylin at 5 μM, 100 μl/well. Cells were aspirated and soluble amylin was added back at 5 μM per 100l/well. For compound studies, 50 μl of 2× compound was added before adding the soluble amylin.

Figure 7:
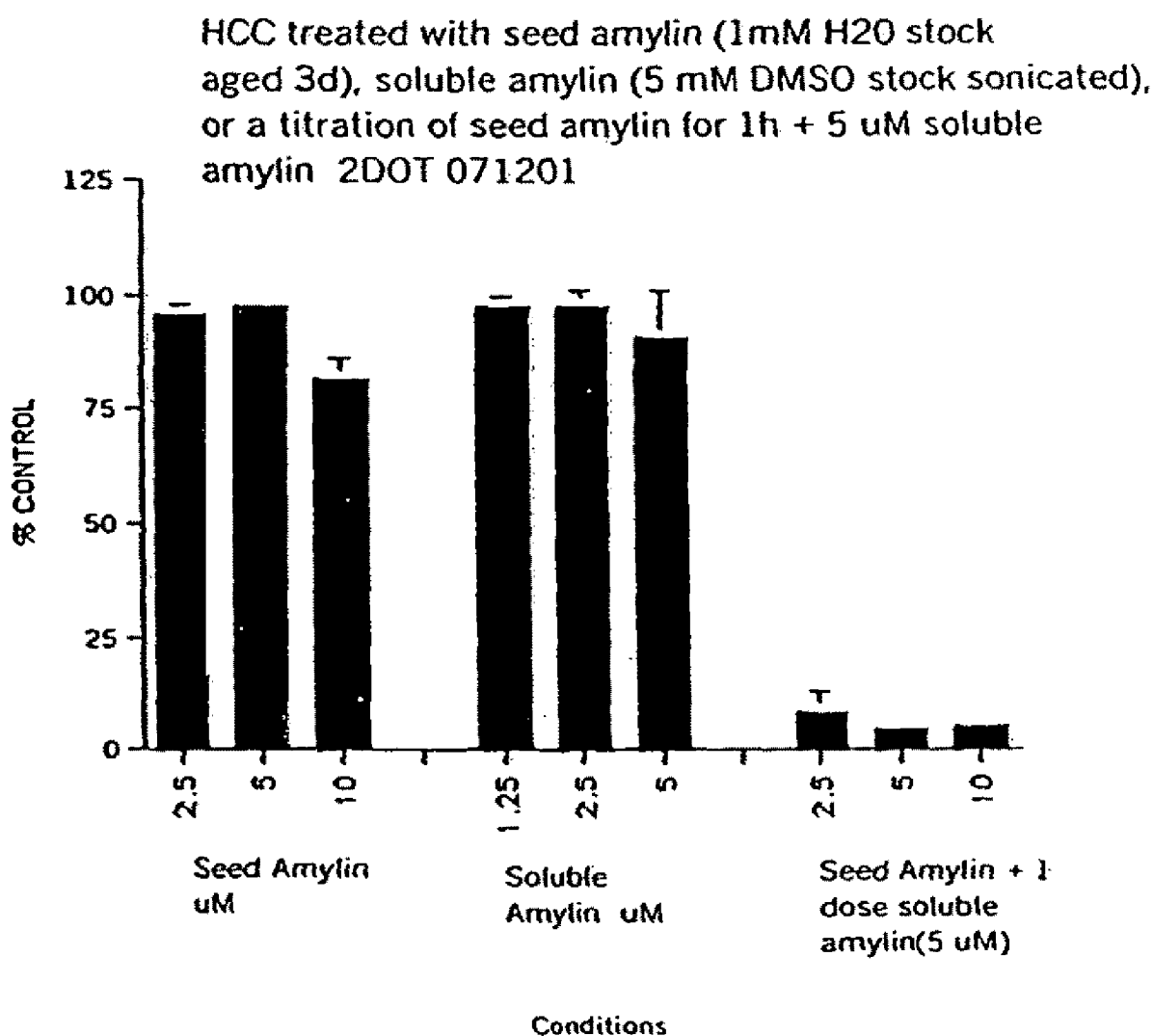
FIG. 7 illustrates toxicity after 1 day when human cortical neurons are seeded for 1 hour followed by aspiration and treatment with soluble amylin. Integrin or integrin subunit antibodies can be added to the cells in the presence of the seed and soluble amylin to inhibit toxicity. Seed and soluble amylin alone are not toxic. However, if cells are seeded for 1 hour followed by aspiration and treatment with amylin, the amylin is toxic.
Figure 8:
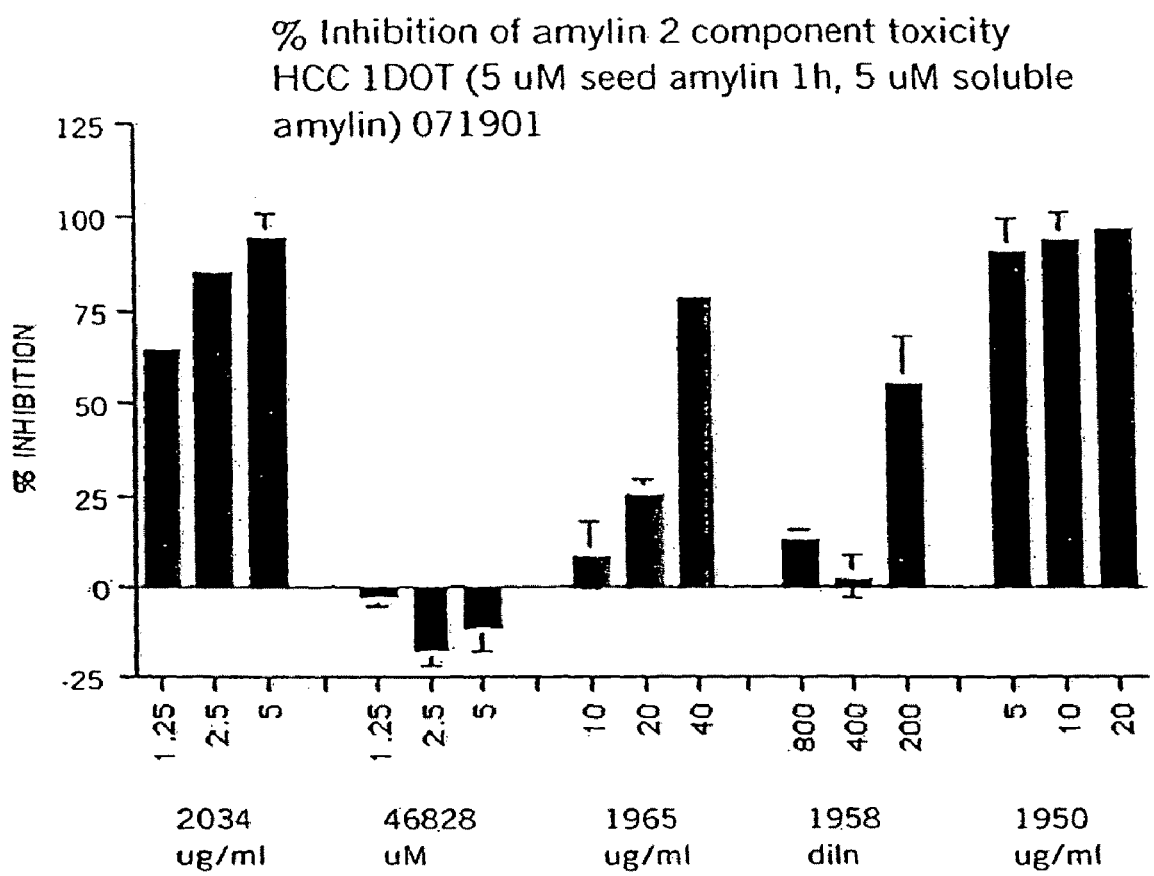
FIG. 8 illustrates that integrin and integrin subunit antibodies, particularly, anti-laminin, anti-β1, anti-αv and anti-α2 antibodies protect against amylin toxicity.
Figure 9A:
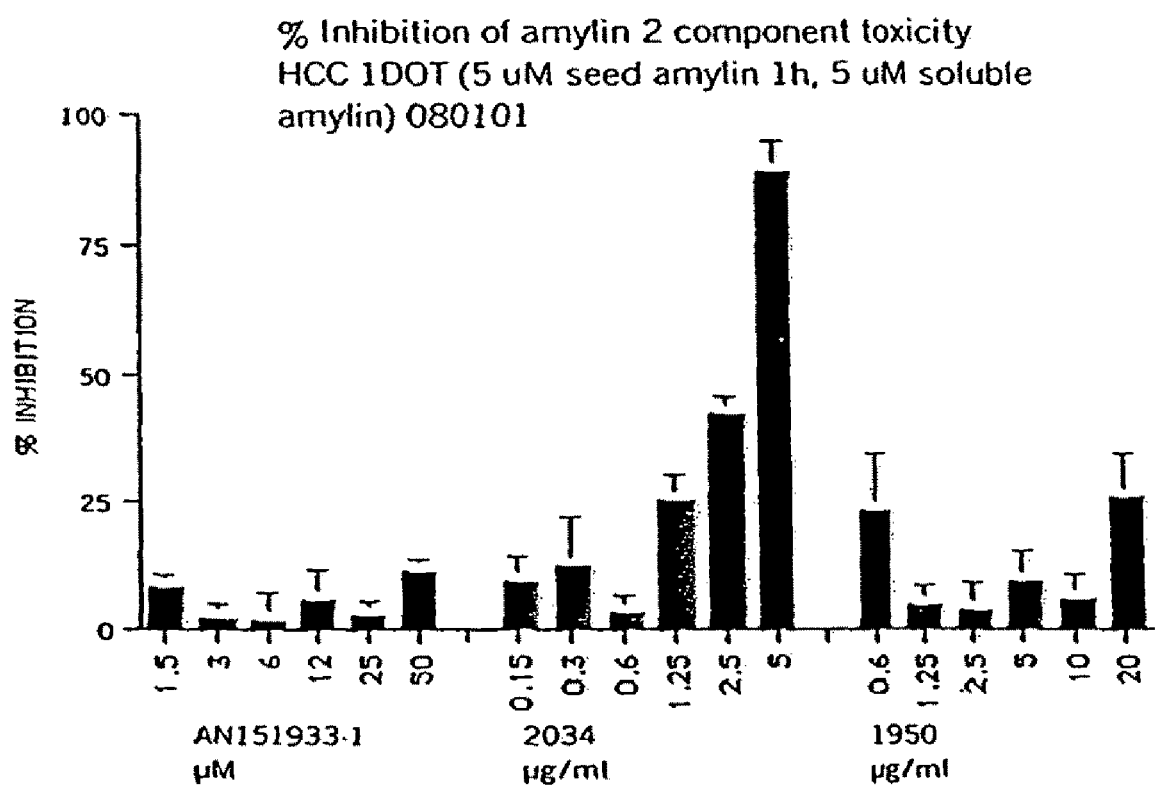
FIGS. 9A and 9B illustrate the effect of integrin or integrin subunit antibodies, including anti-αvβ3 anti-αv; and cytochalasin D, in protecting against amylin toxicity as demonstrated by the percent inhibition of amylin 2 component toxicity after cells are exposed for 1 hour to the seed amylin.
Figure 9B:
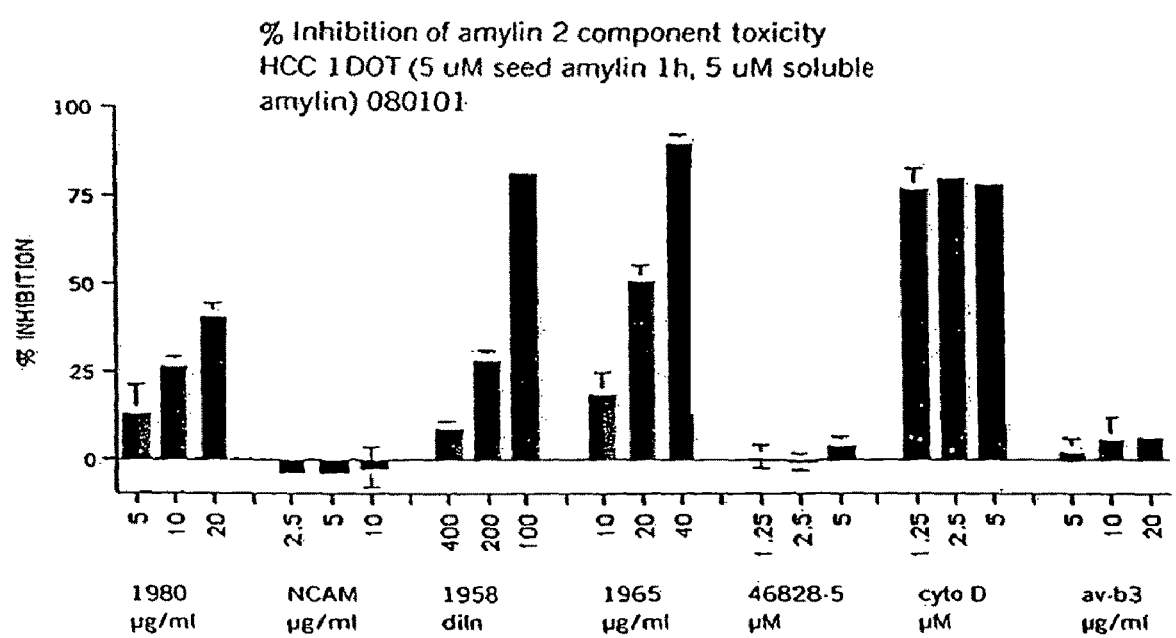

FIG. 6 demonstrates toxicity after 1 day when the human cortical neurons were seeded for 1 hour followed by aspiration and treatment with soluble amylin. Integrin antibodies were added to the cells in the presence of the seed and soluble amylin to inhibit toxicity. FIG. 7 demonstrates that some integrin antibodies, namely 2034 anti-laminin, 1965 anti-β1 integrin, 1958 anti-αv (VNR) and 1950 anti-α2, protected the cells against the toxicity of the amylin two components. FIG. 8 demonstrates that amylin two component toxicity is further inhibited by additional integrin antibodies including anti-αvβ3 and anti-αv; and cytochalasin D.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

---

What is claimed is:

1. A method of treating a patient having an amyloidogenic disease comprising administering an effective dosage of a monoclonal antibody or fragment thereof that binds to an αv subunit when it is a component of an αvβ1 integrin and thereby treating the disease.

2. The method of claim 1, wherein the monoclonal antibody or fragment binds to the integrin αvβ1.

3. The method of claim 1, wherein the monoclonal antibody or fragment inhibits adhesion of αv integrin subunit-expressing cells to vitronectin or fibronectin.

4. The method of claim 1, wherein the monoclonal antibody or fragment inhibits adhesion of αv integrin subunit-expressing cells to osteopontin.

5. The method of claim 1, wherein the monoclonal antibody or fragment recognizes the same epitope as an antibody VNR147 or 1980.

6. The method of claim 1, wherein the monoclonal antibody or fragment competes with an antibody VNR147 or 1980 for binding to αvβ1 integrin.

7. The method of claim 1, wherein the monoclonal antibody or fragment is VNR147 or 1980.

8. The method of claim 1, wherein the monoclonal antibody is a human antibody.

9. The method of claim 1, wherein the monoclonal antibody is a humanized antibody.

10. The method of claim 1, wherein the monoclonal antibody is a mouse antibody.

11. The method of claim 1, wherein the fragment of the monoclonal antibody is administered.

12. The method of claim 11, wherein the fragment is an F(ab), $F(ab)_2$, $F(ab)_c$, or F(v).

13. The method of claim 1, wherein a monoclonal antibody of isotype IgG1 or IgG4 is administered.

14. The method of claim 1, wherein a monoclonal antibody of isotype IgG2 or IgG4 is administered.

15. The method of claim 1, wherein a monoclonal antibody comprising two pairs of light and heavy chains is administered.

16. The method of claim 1, wherein the dosage of the monoclonal antibody or fragment is about 0.01 to about 10 mg/kg body weight of the patient.

17. The method of claim 1, wherein the monoclonal antibody or fragment is administered with a carrier as a pharmaceutical composition.

18. The method of claim 1, wherein the monoclonal antibody or fragment is administered intraperitoneally, orally, intranasally, subcutaneously, intrathecally, intramuscularly, topically or intravenously.

19. The method of claim 1, wherein the monoclonal antibody or fragment inhibits formation of amyloid deposits in the patient.

20. The method of claim 1, wherein the monoclonal antibody or fragment also binds to the αv subunit in free form.

21. The method of claim 1, wherein the disease is Alzheimer's disease.

* * * * *

UNITED STATES PATENT AND TRADEMARK OFFICE
CERTIFICATE OF CORRECTION

PATENT NO. : 7,901,683 B2
APPLICATION NO. : 12/336340
DATED : March 8, 2011
INVENTOR(S) : Irene Griswold-Prenner et al.

Page 1 of 1

It is certified that error appears in the above-identified patent and that said Letters Patent is hereby corrected as shown below:

Claim 4, Column 37, Line 2, delete "av" and insert --$\alpha v$--
Claim 5, Column 37, Line 5, delete "an"
Claim 12, Column 37, Line 21, delete "$F(ab)_c$" and insert --$F(ab)_c$--

Signed and Sealed this
Twenty-sixth Day of July, 2011

David J. Kappos
*Director of the United States Patent and Trademark Office*